US008822644B2

(12) United States Patent
Nash et al.

(10) Patent No.: US 8,822,644 B2
(45) Date of Patent: Sep. 2, 2014

(54) METHOD OF TREATING CANCER COMPRISING A VEGF-B ANTAGONIST

(75) Inventors: Andrew Nash, Kew (AU); Felicity Meredith Dunlop, Regent (AU); Manuel Baca, Viewbank (AU); Louis Jerry Fabri, Diamond Creek (AU); Pierre David Scotney, Greensborough (AU)

(73) Assignee: Zenyth Operations Pty Ltd, Victoria (AU)

( * ) Notice: Subject to any disclaimer, the term of this patent is extended or adjusted under 35 U.S.C. 154(b) by 690 days.

(21) Appl. No.: 11/659,179

(22) PCT Filed: Aug. 2, 2005

(86) PCT No.: PCT/AU2005/001152

§ 371 (c)(1), (2), (4) Date: Feb. 2, 2007

(87) PCT Pub. No.: WO2006/012688

PCT Pub. Date: Feb. 9, 2006

(65) Prior Publication Data

US 2008/0260729 A1 Oct. 23, 2008

(51) Int. Cl.

*C07K 16/22* (2006.01)
*C12P 21/08* (2006.01)
*C12N 5/10* (2006.01)
*C12N 15/13* (2006.01)
*C12N 5/07* (2010.01)
*A61K 39/00* (2006.01)

(52) U.S. Cl.

CPC ............. *C07K 16/22* (2013.01); *C07K 2317/24* (2013.01); *A61K 2039/505* (2013.01); *C07K 2317/55* (2013.01); *C07K 2316/96* (2013.01); *C07K 2317/73* (2013.01)

USPC .................. 530/387.1; 530/387.3; 530/388.1; 530/388.24; 435/69.6; 435/252.3; 435/254.11; 435/320.1; 435/326; 435/328; 435/336

(58) Field of Classification Search

None

See application file for complete search history.

(56) References Cited

U.S. PATENT DOCUMENTS

| | | | | |
|---|---|---|---|---|
| 5,607,918 | A * | 3/1997 | Eriksson et al. | 514/12 |
| 5,916,763 | A * | 6/1999 | Williams et al. | 435/69.1 |
| 6,331,301 | B1 * | 12/2001 | Eriksson et al. | 424/145.1 |
| 6,482,802 | B1 * | 11/2002 | Hu et al. | 514/39 |
| 6,942,981 | B1 * | 9/2005 | Lu et al. | 435/7.1 |
| 7,517,524 | B2 | 4/2009 | Nash et al. | |
| 2003/0170253 | A1 | 9/2003 | Eriksson et al. | |
| 2003/0232439 | A1 | 12/2003 | Zhang et al. | |
| 2004/0005671 | A1 | 1/2004 | Nash et al. | |

FOREIGN PATENT DOCUMENTS

| | | | |
|---|---|---|---|
| JP | 2000-228982 | A | 8/2000 |
| WO | WO91/09967 | * | 7/1991 |
| WO | 00/64261 | A1 | 11/2000 |
| WO | 03/070910 | A2 | 8/2003 |

OTHER PUBLICATIONS

Clark (Protein Engineering of Antibody Molecules for Prophylactic and Therapeutic Applications in Man, 1993, pp. 4-5).*
Rudikoff et al (Proc Natl Acad Sci USA 1982 vol. 79 p. 1979-1983).*
Tolcher et al (Clinical Cancer Research, 2002, vol. 8, pp. 2530-2535).*
Cripps et al (Clinical Cancer Research. 2002, 8, pp. 2188-2192).*
James and Gibson (Blood, 1998, vol. 91, pp. 371-382).*
Scotney et al (Clinical and Experimental Pharmacology and Physiology, 2002, vol. 29, pp. 1024-1029).*
Schlom ('Monoclonal Antibodies: They're More and Less Than You Think', In, Molecular Foundations of Oncology, 1991, S. Broder, Ed., pp. 95-124).*
Panka et al (Proc Natl Acad Sci USA, 1988, vol. 85, pp. 3080-3084).*
Olofsson et al (Current Opinion in Biotechnology, 1999, vol. 10, pp. 525-535).*
Underiner, T.L. et al., "Development of Vascular Endothelial Growth Factor Receptor (VEGFR) Kinase Inhibitors as Anti-Angiogenic Agents in Cancer Therapy", *Current Medicinal Chemistry* 11: 731-745 (2004).
Scotney, PD et al., "Human Vascular Endothelial Growth Factor B: Characterization of Recombinant Isoforms and Generation of Neutralizing Monoclonal Antibodies" *Clinical and Experimental Pharmacology and Physiology* (2002) pp. 1024-1029, vol. 29.
Leonard, P. et al., "Crystal Structure of Vascular Endothelial Growth Factor-B in Complex with a Neutralising Antibody Fab Fragment" *Journal of Molecular Biology* (2008) pp. 1203-1217, vol. 384.
Supplemental European Search Report dated Oct. 19, 2009.
Winkler, K. et al., "Changing the Antigen Binding Specificity by Single Point Mutations of an Anti-p24 (HIV-1) Antibody" The Journal of Immunology, XP-002579393 (Oct. 15, 2000) pp. 4505-4514, vol. 165, No. 8.
European Official Action dated Jul. 27, 2011 issued in corresponding European Application No. 05 764 158.1.
Underiner, T.L. et al., "Development of Vascular Endothelial Growth Factor Receptor (VEGFR) Kinase Inhibitors as Anti-Angiogenic Agents in Cancer Therapy" Current Medicinal Chemistry (Jan. 1, 2004) pp. 731-745, vol. 11.
Partial European Search Report dated Jun. 5, 2012 issued in European Application No. EP 12151292.5.
Zhang, L. et al., "Vector-Based TNAi, a Novel Tool for Isoform-Specific Knock-Down of VEGF and Anti-Angiogenesis Gene Therapy of Cancer" *Biochemical and Biophysical Research Communications* (2003) pp. 1169-1173, vol. 303(4).
Filleur, S. et al., "SiRNA-Mediated Inhibition of Vascular Endothelial Growth Factor Severely Limits Tumor Resistance to Antiangiogenic Thrombospondin-1 and Slows Tumor Vascularization and Growth" *Cancer Research* (2003) pp. 3919-3922, vol. 63(14).
Translation of Japanese Office Action dated Mar. 3, 2011.

* cited by examiner

*Primary Examiner* — Karen Canella
(74) *Attorney, Agent, or Firm* — Scully, Scott, Murphy & Presser, P.C.

(57) ABSTRACT

The present invention relates generally to the field of cancer therapy and prophylaxis. More particularly, the present invention provides growth factor antagonists which inhibit the growth of cancers including tumors and pre-cancerous tissue. Even more particularly, the present invention is directed to antagonists of vascular endothelial growth factor-B and their use to inhibit the growth of cancer including tumor tissue and pre-cancerous tissue.

29 Claims, 7 Drawing Sheets

2H10 light chain variable region

```
         10        20        30        40
EIQMTQTTSSLSASLGDRVTISCRASQDISNFLNWYQQKP

         50        60        70        80
DGTVKLLIYYTSTLHSGVPSRFSGSGSGTDYSLTISNLEQ

         90       100
EDIATYFCQQGKTLPPTFGGGTKLEIK
```

2H10 heavy chain variable region

```
         10        20        30        40
QVQLQQPGTELVKPGASVKLSCKASGYTFTGFWIHWVKQR

         50  a       60        70        80
PGQGLEWIGHINPGNGGTNYNEKFKRMATLTVDKSSSTAYM

  abc      90       100abc      110
QLSSLTSEDSAVYYCARSYSNYVRAMDYWGQGTSVTVSS
```

Figure 1

4E12 light chain variable region

```
        10        20        30        40
DIVMTQSQKFMSSSVGDRVSVTCKASQNVNTNVAWYQQKQ

        50        60        70        80
GQSPRPLIYSASSRCSGVPDRFTGSGFGTDFTLTISNVQS

        90        100
EDLAEYFCQQYHSFPLTFGAGAKLDLK
```

4E12 heavy chain variable region

```
        10        20        30        40
QVQPQQPGAELVKPGASVKMSCKASGDTFTNSWIGWVTQR

        50 a       60         70        80
PGQGLEWIGDIFPGSGHTNYNEKFKNRATLTVDTSSSTAYM

  abc      90       100       110
LLSSLTSDDSAVYYCVIENYAWFAYWGQGTLVTVSA
```

Figure 2

2F5 light chain variable region 10 20 30 40
DIVMTQSHKFMSTSVGDRVSITCKASQDVGTAVAWYQQKP 50 60 70 80
GQSPKLLIYWASTRHTGVPDRFTGSGSGTDFTLTISNVQS 90 100
EDLADYFCQQYSSSLTFGAGATKLELK 2F5 heavy chain variable region 10 20 30 40
QVQLQQSGPELVKPGTSVRISCKASGYTFTTFYIHWVKQR 50 a 60 70 80
PGQGLEWIGWFYPGNVNTNYNEKLKGKATLTADKSSSAAYL abc 90 100ab 110
QLNSLTSEDSAVYFCTRSPYYGYVFDYWGQGTTLTVSS

Figure 3

Human Variable Light Chain: Germline PK9/JK4

DIQMTQSPSSLSASVGDRVTITCRASQSISYFLNWYQQKPGKAPKLLIYAASSLQSGVPS
RFSGSGSGTDFTLTISSLQPEDFATYYCQQSYSTPPTFGGGTKVEIK

Human Variable Heavy Chain: Germline DP75/JH4a

QVQLVQSGAEVKKPGASVKVSCKASGYTFTGYYMHWVRQAPGQGLEWMGWINPNSGGTNY
AQKFQGRVTMTRDTSISTAYMELSRLRSDDTAVYYCARSYSNYVRYFDYWGQGTLVTVSS

Figure 4

2H10 CDR-Grafted Human Variable Light Chain: Germline PK9/JK4

DIQMTQSPSSLSASVGDRVTITCRASQDISNFLNWYQQKPGKAPKLLIYYTSTLHSGVPS
RFSGSGSGTDFTLTISSLQPEDFATYYCQQGKTLPPTFGGGTKVEIK

2H10 CDR-Grafted Human Variable Heavy Chain: Germline DP75/JH4a

QVQLVQSGAEVKKPGASVKVSCKASGYTFTGFWIHWVRQAPGQGLEWMGHINPGNGGTNY
NEKFKRRVTMTRDKSISTAYMELSRLRSDDTAVYYCARSYSNYVRAMDYWGQGTLVTVSS

Figure 5

2H10 $V_L$ Chain CDR Regions

CDR-L1
AGGGCAAGTCAGGACATTAGCAATTTTTTAAAC (murine)

CGTGCGAGCCAGGATATTAGCAACTTTCTGAAC (E.coli)

CDR-L2
TACACATCAACATTACACTCA (murine)

TATACCAGCACCCTGCATAGC (E.coli)

CDR-L3
CAACAGGGTAAAACGCTTCCTCCCACG (murine)

CAGCAGGGCAAAACCCTGCCGCCGACC (E.coli)

2H10 $V_H$ Chain CDR Regions

CDR-H1
GGCTACACTTTCACTGGCTTCTGGATACAC (murine)

GGCTATACCTTTACCGGCTTTTGGATTCAT (E.coli)

CDR-H2
CATATTAATCCTGGCAATGGTGGCACTAACTACAATGAGAAGTTCAAGAGA (murine)

CATATTAACCCGGGCAACGGCGGTACCAACTATAACGAAAAATTTAAACGT (E.coli)

CDR-H3
TCCTATAGTAACTACGTGCGGGCTATGGACTAC (murine)

AGCTATAGCAACTATGTGCGTGCGATGGATTAT (E.coli)

Figure 6

1C6 light chain variable region 10 20 30 40
DIVMTQSHKFMSTSVGDRVSITCKASQDVGSAVAWYQQKP 50 60 70 80
GQSPKLLIYWASTRHTGVPDRFTGSGSGTDFTFTISNVQS 90 100
EDLADYFCQQYSSSLTFGAGATKLELK 1C6 heavy chain variable region 10 20 30 40
QVQLQQSGPELVKPGASVRISCKASGYTFTTFYIHWVKQR 50 a 60 70 80
PGQGLEWIAWFYPGNVNTNYNEKFKDKATLTADKSSSAAYL abc 90 100ab 110
QLNSLTSEDSAVYFCTRSPYYGYVFDFWGQGTTLTVSS

Figure 7

SEQUENCE LISTING

```
<160> NUMBER OF SEQ ID NOS: 50

<210> SEQ ID NO 1
<211> LENGTH: 99
<212> TYPE: PRT
<213> ORGANISM: human

<400> SEQUENCE: 1

His Gln Arg Lys Val Val Ser Trp Ile Asp Val Tyr Thr Arg Ala Thr
1               5                   10                  15

Cys Gln Pro Arg Glu Val Val Val Pro Leu Thr Val Glu Leu Met Gly
            20                  25                  30

Thr Val Ala Lys Gln Leu Val Pro Ser Cys Val Thr Val Gln Arg Cys
        35                  40                  45

Gly Gly Cys Cys Pro Asp Asp Gly Leu Glu Cys Val Pro Thr Gly Gln
    50                  55                  60

His Gln Val Arg Met Gln Ile Leu Met Ile Arg Tyr Pro Ser Ser Gln
65                  70                  75                  80

Leu Gly Glu Met Ser Leu Glu Glu His Ser Gln Cys Glu Cys Arg Pro
                85                  90                  95

Lys Lys Lys


<210> SEQ ID NO 2
<211> LENGTH: 99
<212> TYPE: PRT
<213> ORGANISM: murine

<400> SEQUENCE: 2

His Gln Lys Lys Val Val Pro Trp Ile Asp Val Tyr Ala Arg Ala Thr
```

-continued

```
1               5                   10                  15

Cys Gln Pro Arg Glu Val Val Val Pro Leu Ser Met Glu Leu Met Gly
            20                  25                  30

Asn Val Val Lys Gln Leu Val Pro Ser Cys Val Thr Val Gln Arg Cys
        35                  40                  45

Gly Gly Cys Cys Pro Asp Asp Gly Leu Glu Cys Val Pro Thr Gly Gln
    50                  55                  60

His Gln Val Arg Met Gln Ile Leu Met Ile Gln Tyr Pro Ser Ser Gln
65                  70                  75                  80

Leu Gly Glu Met Ser Leu Glu Glu His Ser Gln Cys Glu Cys Arg Pro
                85                  90                  95

Lys Lys Lys


<210> SEQ ID NO 3
<211> LENGTH: 107
<212> TYPE: PRT
<213> ORGANISM: murine

<400> SEQUENCE: 3

Glu Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
            20                  25                  30

Leu Asn Trp Tyr Gln Gln Lys Pro Asp Gly Thr Val Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Thr Leu Pro Pro
                85                  90                  95

Thr Phe Gly Gly Gly Thr Lys Leu Glu Ile Lys
            100                 105


<210> SEQ ID NO 4
<211> LENGTH: 120
<212> TYPE: PRT
<213> ORGANISM: murine

<400> SEQUENCE: 4

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Gly Phe
            20                  25                  30

Trp Ile His Trp Val Lys Gln Arg Pro Gly Gln Gly Leu Glu Trp Ile
        35                  40                  45

Gly His Ile Asn Pro Gly Asn Gly Gly Thr Asn Tyr Asn Glu Lys Phe
    50                  55                  60

Lys Arg Met Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Tyr Ser Asn Tyr Val Arg Ala Met Asp Tyr Trp Gly Gln
            100                 105                 110

Gly Thr Ser Val Thr Val Ser Ser
        115                 120
```

<210> SEQ ID NO 5
<211> LENGTH: 11
<212> TYPE: PRT
<213> ORGANISM: murine

<400> SEQUENCE: 5

Arg Ala Ser Gln Asp Ile Ser Asn Phe Leu Asn
1 5 10

<210> SEQ ID NO 6
<211> LENGTH: 7
<212> TYPE: PRT
<213> ORGANISM: murine

<400> SEQUENCE: 6

Tyr Thr Ser Thr Leu His Ser
1 5

<210> SEQ ID NO 7
<211> LENGTH: 9
<212> TYPE: PRT
<213> ORGANISM: murine

<400> SEQUENCE: 7

Gln Gln Gly Lys Thr Leu Pro Pro Thr
1 5

<210> SEQ ID NO 8
<211> LENGTH: 10
<212> TYPE: PRT
<213> ORGANISM: murine

<400> SEQUENCE: 8

Gly Tyr Thr Phe Thr Gly Phe Trp Ile His
1 5 10

<210> SEQ ID NO 9
<211> LENGTH: 17
<212> TYPE: PRT
<213> ORGANISM: murine

<400> SEQUENCE: 9

His Ile Asn Pro Gly Asn Gly Gly Thr Asn Tyr Asn Glu Lys Phe Lys
1 5 10 15

Arg

<210> SEQ ID NO 10
<211> LENGTH: 11
<212> TYPE: PRT
<213> ORGANISM: murine

<400> SEQUENCE: 10

Ser Tyr Ser Asn Tyr Val Arg Ala Met Asp Tyr
1 5 10

<210> SEQ ID NO 11
<211> LENGTH: 107
<212> TYPE: PRT
<213> ORGANISM: murine

<400> SEQUENCE: 11

Asp Ile Val Met Thr Gln Ser Gln Lys Phe Met Ser Ser Ser Val Gly
1 5 10 15

-continued

```
Asp Arg Val Ser Val Thr Cys Lys Ala Ser Gln Asn Val Asn Thr Asn
            20                  25                  30

Val Ala Trp Tyr Gln Gln Lys Gln Gly Gln Ser Pro Arg Pro Leu Ile
        35                  40                  45

Tyr Ser Ala Ser Ser Arg Cys Ser Gly Val Pro Asp Arg Phe Thr Gly
    50                  55                  60

Ser Gly Phe Gly Thr Asp Phe Thr Leu Thr Ile Ser Asn Val Gln Ser
65                  70                  75                  80

Glu Asp Leu Ala Glu Tyr Phe Cys Gln Gln Tyr His Ser Phe Pro Leu
                85                  90                  95

Thr Phe Gly Ala Gly Ala Lys Leu Asp Leu Lys
            100                 105


<210> SEQ ID NO 12
<211> LENGTH: 117
<212> TYPE: PRT
<213> ORGANISM: murine

<400> SEQUENCE: 12

Gln Val Gln Pro Gln Gln Pro Gly Ala Glu Leu Val Lys Pro Gly Ala
1               5                   10                  15

Ser Val Lys Met Ser Cys Lys Ala Ser Gly Asp Thr Phe Thr Asn Ser
            20                  25                  30

Trp Ile Gly Trp Val Thr Gln Arg Pro Gly Gln Gly Leu Glu Trp Ile
        35                  40                  45

Gly Asp Ile Phe Pro Gly Ser Gly His Thr Asn Tyr Asn Glu Lys Phe
    50                  55                  60

Lys Asn Arg Ala Thr Leu Thr Val Asp Thr Ser Ser Ser Thr Ala Tyr
65                  70                  75                  80

Met Leu Leu Ser Ser Leu Thr Ser Asp Asp Ser Ala Val Tyr Tyr Cys
                85                  90                  95

Val Ile Glu Asn Tyr Ala Trp Phe Ala Tyr Trp Gly Gln Gly Thr Leu
            100                 105                 110

Val Thr Val Ser Ala
        115


<210> SEQ ID NO 13
<211> LENGTH: 11
<212> TYPE: PRT
<213> ORGANISM: murine

<400> SEQUENCE: 13

Lys Ala Ser Gln Asn Val Asn Thr Asn Val Ala
1               5                   10


<210> SEQ ID NO 14
<211> LENGTH: 7
<212> TYPE: PRT
<213> ORGANISM: murine

<400> SEQUENCE: 14

Ser Ala Ser Ser Arg Cys Ser
1               5


<210> SEQ ID NO 15
<211> LENGTH: 9
<212> TYPE: PRT
<213> ORGANISM: murine
```

<400> SEQUENCE: 15

Gln Gln Tyr His Ser Phe Pro Leu Thr
1               5

<210> SEQ ID NO 16
<211> LENGTH: 10
<212> TYPE: PRT
<213> ORGANISM: murine

<400> SEQUENCE: 16

Gly Asp Thr Phe Thr Asn Ser Trp Ile Gly
1               5                   10

<210> SEQ ID NO 17
<211> LENGTH: 17
<212> TYPE: PRT
<213> ORGANISM: murine

<400> SEQUENCE: 17

Asp Ile Phe Pro Gly Ser Gly His Thr Asn Tyr Asn Glu Lys Phe Lys
1               5                   10                  15

Asn

<210> SEQ ID NO 18
<211> LENGTH: 8
<212> TYPE: PRT
<213> ORGANISM: murine

<400> SEQUENCE: 18

Glu Asn Tyr Ala Trp Phe Ala Tyr
1               5

<210> SEQ ID NO 19
<211> LENGTH: 107
<212> TYPE: PRT
<213> ORGANISM: murine

<400> SEQUENCE: 19

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Ser Leu Thr
                85                  90                  95

Phe Gly Ala Gly Ala Thr Lys Leu Glu Leu Lys
            100                 105

<210> SEQ ID NO 20
<211> LENGTH: 119
<212> TYPE: PRT
<213> ORGANISM: murine

<400> SEQUENCE: 20

Gln Val Gln Leu Gln Gln Ser Gly Pro Glu Leu Val Lys Pro Gly Thr
1               5                   10                  15

Ser Val Arg Ile Ser Cys Lys Ala Ser Gly Tyr Thr Phe Thr Thr Phe
20 25 30

Tyr Ile His Trp Val Lys Gln Arg Pro Gly Gln Gly Leu Glu Trp Ile
35 40 45

Gly Trp Phe Tyr Pro Gly Asn Val Asn Thr Asn Tyr Asn Glu Lys Leu
50 55 60

Lys Gly Lys Ala Thr Leu Thr Ala Asp Lys Ser Ser Ser Ala Ala Tyr
65 70 75 80

Leu Gln Leu Asn Ser Leu Thr Ser Glu Asp Ser Ala Val Tyr Phe Cys
85 90 95

Thr Arg Ser Pro Tyr Tyr Gly Tyr Val Phe Asp Tyr Trp Gly Gln Gly
100 105 110

Thr Thr Leu Thr Val Ser Ser
115

<210> SEQ ID NO 21
<211> LENGTH: 11
<212> TYPE: PRT
<213> ORGANISM: murine

<400> SEQUENCE: 21

Lys Ala Ser Gln Asp Val Gly Thr Ala Val Ala
1 5 10

<210> SEQ ID NO 22
<211> LENGTH: 7
<212> TYPE: PRT
<213> ORGANISM: murine

<400> SEQUENCE: 22

Trp Ala Ser Thr Arg His Thr
1 5

<210> SEQ ID NO 23
<211> LENGTH: 8
<212> TYPE: PRT
<213> ORGANISM: murine

<400> SEQUENCE: 23

Gln Gln Tyr Ser Ser Ser Leu Thr
1 5

<210> SEQ ID NO 24
<211> LENGTH: 10
<212> TYPE: PRT
<213> ORGANISM: murine

<400> SEQUENCE: 24

Gly Tyr Thr Phe Thr Thr Phe Tyr Ile His
1 5 10

<210> SEQ ID NO 25
<211> LENGTH: 17
<212> TYPE: PRT
<213> ORGANISM: murine

<400> SEQUENCE: 25

Trp Phe Tyr Pro Gly Asn Val Asn Thr Asn Tyr Asn Glu Lys Leu Lys
1 5 10 15

Gly

```
<210> SEQ ID NO 26
<211> LENGTH: 10
<212> TYPE: PRT
<213> ORGANISM: murine

<400> SEQUENCE: 26

Ser Pro Tyr Tyr Gly Tyr Val Phe Asp Tyr
1               5                   10


<210> SEQ ID NO 27
<211> LENGTH: 107
<212> TYPE: PRT
<213> ORGANISM: murine

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Tyr Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gly Gly Thr Lys Val Glu Ile Lys
            100                 105


<210> SEQ ID NO 28
<211> LENGTH: 120
<212> TYPE: PRT
<213> ORGANISM: human

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Tyr Ser Asn Tyr Val Arg Tyr Phe Asp Tyr Trp Gly Gln
            100                 105                 110

Gly Thr Leu Val Thr Val Ser Ser
        115                 120


<210> SEQ ID NO 29
<211> LENGTH: 107
<212> TYPE: PRT
<213> ORGANISM: human

<400> SEQUENCE: 29
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Lys Thr Leu Pro Pro
                85                  90                  95

Thr Phe Gly Gly Gly Thr Lys Val Glu Ile Lys
            100                 105


<210> SEQ ID NO 30
<211> LENGTH: 120
<212> TYPE: PRT
<213> ORGANISM: human

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Phe
            20                  25                  30

Trp Ile His Trp Val Arg Gln Ala Pro Gly Gln Gly Leu Glu Trp Met
        35                  40                  45

Gly His Ile Asn Pro Gly Asn Gly Gly Thr Asn Tyr Asn Glu Lys Phe
    50                  55                  60

Lys Arg Arg Val Thr Met Thr Arg Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Tyr Ser Asn Tyr Val Arg Ala Met Asp Tyr Trp Gly Gln
            100                 105                 110

Gly Thr Leu Val Thr Val Ser Ser
        115                 120


<210> SEQ ID NO 31
<211> LENGTH: 33
<212> TYPE: DNA
<213> ORGANISM: murine

<400> SEQUENCE: 31

agggcaagtc aggacattag caatttttta aac                                 33


<210> SEQ ID NO 32
<211> LENGTH: 33
<212> TYPE: DNA
<213> ORGANISM: E. coli

<400> SEQUENCE: 32

cgtgcgagcc aggatattag caactttctg aac                                 33


<210> SEQ ID NO 33
<211> LENGTH: 21
<212> TYPE: DNA
<213> ORGANISM: murine
```

<400> SEQUENCE: 33
tacacatcaa cattacactc a 21

<210> SEQ ID NO 34
<211> LENGTH: 21
<212> TYPE: DNA
<213> ORGANISM: E. coli

<400> SEQUENCE: 34
tataccagca ccctgcatag c 21

<210> SEQ ID NO 35
<211> LENGTH: 27
<212> TYPE: DNA
<213> ORGANISM: murine

<400> SEQUENCE: 35
caacagggta aaacgcttcc tcccacg 27

<210> SEQ ID NO 36
<211> LENGTH: 27
<212> TYPE: DNA
<213> ORGANISM: E. coli

<400> SEQUENCE: 36
cagcagggca aaaccctgcc gccgacc 27

<210> SEQ ID NO 37
<211> LENGTH: 30
<212> TYPE: DNA
<213> ORGANISM: murine

<400> SEQUENCE: 37
ggctacactt tcactggctt ctggatacac 30

<210> SEQ ID NO 38
<211> LENGTH: 30
<212> TYPE: DNA
<213> ORGANISM: E. coli

<400> SEQUENCE: 38
ggctatacct ttaccggctt ttggattcat 30

<210> SEQ ID NO 39
<211> LENGTH: 51
<212> TYPE: DNA
<213> ORGANISM: murine

<400> SEQUENCE: 39
catattaatc ctggcaatgg tggcactaac tacaatgaga agttcaagag a 51

<210> SEQ ID NO 40
<211> LENGTH: 51
<212> TYPE: DNA
<213> ORGANISM: E. coli

<400> SEQUENCE: 40
catattaacc cgggcaacgg cggtaccaac tataacgaaa aatttaaacg t 51

<210> SEQ ID NO 41
<211> LENGTH: 33
<212> TYPE: DNA

<213> ORGANISM: murine

<400> SEQUENCE: 41
tcctatagta actacgtgcg ggctatggac tac 33

<210> SEQ ID NO 42
<211> LENGTH: 33
<212> TYPE: DNA
<213> ORGANISM: E. coli

<400> SEQUENCE: 42
agctatagca actatgtgcg tgcgatggat tat 33

<210> SEQ ID NO 43
<211> LENGTH: 106
<212> TYPE: PRT
<213> ORGANISM: murine

<400> SEQUENCE: 43

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Phe Thr Ile Ser Asn Val Gln Ser
65                  70                  75                  80

Glu Asp Leu Ala Asp Tyr Phe Cys Gln Gln Tyr Ser Ser Ser Leu Thr
                85                  90                  95

Phe Gly Ala Gly Ala Thr Lys Leu Glu Leu
            100                 105
```

<210> SEQ ID NO 44
<211> LENGTH: 119
<212> TYPE: PRT
<213> ORGANISM: murine

<400> SEQUENCE: 44

```
Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Thr Phe
            20                  25                  30

Tyr Ile His Trp Val Lys Gln Arg Pro Gly Gln Gly Leu Glu Trp Ile
        35                  40                  45

Ala Trp Phe Tyr Pro Gly Asn Val Asn Thr Asn Tyr Asn Glu Lys Phe
    50                  55                  60

Lys Asp Lys Ala Thr Leu Thr Ala Asp Lys Ser Ser Ser Ala Ala Tyr
65                  70                  75                  80

Leu Gln Leu Asn Ser Leu Thr Ser Glu Asp Ser Ala Val Tyr Phe Cys
                85                  90                  95

Thr Arg Ser Pro Tyr Tyr Gly Tyr Val Phe Asp Phe Trp Gly Gln Gly
            100                 105                 110

Thr Thr Leu Thr Val Ser Ser
        115
```

<210> SEQ ID NO 45

-continued

```
<211> LENGTH: 11
<212> TYPE: PRT
<213> ORGANISM: murine

<400> SEQUENCE: 45

Lys Ala Ser Gln Asp Val Gly Ser Ala Val Ala
1               5                   10


<210> SEQ ID NO 46
<211> LENGTH: 7
<212> TYPE: PRT
<213> ORGANISM: murine

<400> SEQUENCE: 46

Trp Ala Ser Thr Arg His Thr
1               5


<210> SEQ ID NO 47
<211> LENGTH: 8
<212> TYPE: PRT
<213> ORGANISM: murine

<400> SEQUENCE: 47

Gln Gln Tyr Ser Ser Ser Leu Thr
1               5


<210> SEQ ID NO 48
<211> LENGTH: 10
<212> TYPE: PRT
<213> ORGANISM: murine

<400> SEQUENCE: 48

Gly Tyr Thr Phe Thr Thr Phe Tyr Ile His
1               5                   10


<210> SEQ ID NO 49
<211> LENGTH: 17
<212> TYPE: PRT
<213> ORGANISM: murine

<400> SEQUENCE: 49

Trp Phe Tyr Pro Gly Asn Val Asn Thr Asn Tyr Asn Glu Lys Phe Lys
1               5                   10                  15

Asp


<210> SEQ ID NO 50
<211> LENGTH: 10
<212> TYPE: PRT
<213> ORGANISM: murine

<400> SEQUENCE: 50

Ser Pro Tyr Tyr Gly Tyr Val Phe Asp Phe
1               5                   10
```

METHOD OF TREATING CANCER COMPRISING A VEGF-B ANTAGONIST

CROSS-REFERENCE TO RELATED APPLICATIONS

This application is a 371 national phase of PCT/AU2005/001152, having an international filing date of Aug. 2, 2005, which claims priority from U.S. Provisional Application No. 60/598,159, filed on Aug. 2, 2004 and U.S. Provisional Application No. 60/634,444, filed on Dec. 9, 2004.

BACKGROUND OF THE INVENTION

1. Field of the Invention

The present invention relates generally to the field of cancer therapy and prophylaxis. More particularly, the present invention provides growth factor antagonists which inhibit the growth of cancers including tumors and pre-cancerous tissue. Even more particularly, the present invention is directed to antagonists of vascular endothelial growth factor-B and their use to inhibit the growth of cancer including tumor tissue and pre-cancerous tissue.

2. Description of the Prior Art

Bibliographic details of the publications referred to in this specification are also collected at the end of the description.

Reference to any prior art is not, and should not be taken as an acknowledgement or any form of suggestion that this prior art forms part of the common general knowledge in any country.

The development of blood vessels and of vascular supply is a fundamental requirement for organ development and differentiation during embryogenesis, as well as for normal post-natal physiological processes such as wound healing, tissue and organ regeneration, and cyclical growth of the corpus luteum and endometrium (Folkman & Klagsbrun, *Science,* 235(4787): 442-447, 1987; Klagsbrun & D'Amore., *Ann. Rev. Physiol.* 53:217-239, 1991; Carmeliet et al., *Nature* 380: 435-439, 1996; Ferrara et al., *Nature* 380:439-442, 1996). The growth and maturation of new vessels (angiogenesis) is a highly complex and coordinated process and requires the sequential activation of a series of receptors by numerous ligands (Yancopoulos et al., *Nature* 407:242-248, 2000; Ferrara and Alitalo, *Nature Medicine* 5:1359-1364, 1999; Carmeliet, *Nature* 407:249-257, 2000). Vascular endothelial growth factor (VEGF or VEGF-A) is arguably the most thoroughly characterized of these ligands and VEGF-A signaling appears to represent a critical rate-limiting step in the process (Ferrara et al., *Nature Medicine* 9:669-676, 2003).

In addition to normal physiological processes, the pathological growth of tumors is also known to be dependent on the degree of new blood vessel formation in the tumor bed (Carmeliet et al., 2000 supra; Folkman, *Nature Medicine* 1:27-31, 1995; Hanahan & Folkman, *Cell* 86:353-364, 1996). VEGF-A mRNA is upregulated in many human tumors and VEGF-A appears to be an important angiogenic factor frequently utilized by tumors to switch on blood vessel growth (Dvorak et al., *Semin Perinatol* 24:75-78, 2000; Ferrara & Alitalo, 1999 supra; Yancopoulos, 2000 supra; Benjamin & Keshet, *Proc Natl Acad Sci USA* 94:8761-8766, 1997; Ferrara and Davis-Smyth, *Endocr. Rev* 18:4-25, 1997). VEGF-A also increases vascular permeability, and this is thought to be important for tumor invasion and metastasis (Dvorak et at., *Curr Top Microbiol Immunol* 237:97-132, 1999). As a result there has been a significant effort towards the development of agents that target angiogenic factors such as VEGF-A in order to inhibit tumor growth (Ferrara et al., 2003 supra). One such agent is bevacizumab, a humanized mouse monoclonal antibody that binds to, and inhibits the activity of, VEGF-A. Bevacizumab (Avastin) has recently been approved by the FDA for the treatment of colorectal cancer.

VEGF-A is now recognized as the founding member of a family of structurally related molecules. The 'VEGF family' comprises six members including prototype VEGF-A, placenta growth factor (PLGF), VEGF-B, VEGF-C, VEGF-D and VEGF-E (Eriksson & Alitalo, *Curr Top Microbiol Immunol* 237:41-57, 1999). The biological functions of the VEGF family are mediated by the differential activation of at least three structurally homologous tyrosine kinase receptors, VEGFR-1/Flt-1, VEGFR-2/Flk-1/KDR and VEGFR-3/Flt-4. VEGF-A, VEGF-B and PLGF also bind to the non-tyrosine kinase receptors neuropilin-1 and -2, Soker et al., *Cell* 92:735-45, 1998; Neufeld et al., *Trends Cardiovasc Med.* 12:13-19, 2002). According to their receptor binding patterns, the VEGF family can be divided into three subgroups: (1) VEGF-A, which binds to VEGFR-1 and VEGFR-2; (2) PLGF and VEGF-B, which bind only to VEGFR-1 and; (3) VEGF-C and VEGF-D, which interact with both VEGFR-2 and VEGFR-3 (Ferrara & Alitalo, 1999 supra; Ferrara et al., 2003 supra).

As noted above, VEGF-A is the most thoroughly characterized member of the VEGF family and an accumulation of evidence has led to the conclusion that VEGFR-2 is the major mediator of VEGF-A associated biological activities such as endothelial cell proliferation, migration and survival, angiogenesis and vascular permeability (Ferrara et al., 2003 supra). In addition to VEGFR-2, VEGF-C and -D also bind to, and activate, VEGFR-3. VEGFR-3 is expressed primarily on lymphatic endothelial cells and VEGF-C and -D are thought to be key regulators of lymphatic angiogenesis [or lymphangiogenesis] (Makinen et al., *Nature Medicine* 7:199-205, 2001; Skobe et al., *Nature Medicine* 7:192-8, 2001; Stacker et al., *Nature Medicine* 7:186-91, 2001). In contrast to VEGF-A, -C and -D and the downstream effects of signaling through VEGFR-2 or -3, the precise role of VEGF-B and signaling through VEGFR-1 remains poorly understood.

VEGFR-1 is expressed on a variety of cell types (Clauss et al., *J. Biol. Chem.* 271:17629-17634, 1996; Wang & Keiser, *Circ. Res.* 83:832-840, 1998; Niida et al., *J. Exp. Med.* 190: 293-298, 1999) and expression, at least on endothelial cells, is upregulated by hypoxia and a HIF-1$\alpha$ dependent mechanism (Gerber et al., *J. Biol. Chem.* 272:23659-23667, 1997). However, only weak autophosphorylation of VEGFR-1 is observed in response to VEGF-A, and VEGF-A binding to VEGFR-1 appears not to activate the downstream signals required for key endothelial cell responses such as proliferation and survival (de Vries et al., *Science* 255:989-991, 1992; Waltenberger et al., *J. Biol. Chem.* 269:26988-26995, 1994; Keyt et al., *J. Biol. Chem.* 271:5638-5646, 1996; Rahimi et al., *J. Biol. Chem.* 275:16986-16992, 2000). The observation that the VEGFR-1 specific ligand, PLGF, enhanced the activity of VEGF-A on endothelial cells suggested that VEGFR-1 might function as a decoy receptor ie. PLGF displaced VEGF-A from VEGFR-1 making it available to bind to, and signal through VEGFR-2 (Park et al., *J Biol. Chem.* 269: 25646-25654, 1994). In vivo data from genetically modified mice further suggested a non-signaling decoy role for VEGFR-1. VEGFR-1$^{-/-}$ mice died in utero between days 8.5 and 9.5 and although endothelial cells developed, they failed to organize into vascular channels (Fong et al., *Development* 126:3015-3025, 1999). Lethality was attributed to excessive angioblast proliferation and this in turn, was attributed to enhanced VEGF-A action (Fong et al., 1999 supra). The observation that mice expressing VEGFR-1 lacking the kinase domain were healthy and showed no overt defect in vascular development provided further support for the decoy hypothesis, as the truncated receptor could still bind VEGF-A, but not transmit intracellular signals (Hiratsuka et al., *Proc. Natl. Acad. Sci. USA* 4:9349-9354, 1998).

Analysis of VEGF-$B^{-/-}$ mice has also failed to resolve the confusion surrounding the precise physiological (and pathological) role of VEGFR-1 specific ligands and VEGFR-1 signaling. In contrast to VEGF-$A^{-/-}$ mice, VEGF-$B^{-/-}$ mice display no overt defects in vascular development and are healthy and fertile (Bellomo et al., *Circ. Res.* 86:E29-E35, 2000). In one report the hearts of VEGF-$B^{-/-}$ mice were reduced in size and the response to coronary occlusion and myocardial recovery from ischemia were compromised (Bellomo et al 2000, supra). Although heart morphology appeared normal, the authors concluded that VEGF-B is essential for the establishment of a fully functional coronary vasculature. In contrast, a second report describing VEGF-$B^{-/-}$ mice reported only a minor atrial conduction defect (Aase et al., *Circulation* 104:358-364, 2001).

As a result of the confusion surrounding the role for VEGFR-1 and VEGFR-1-specific ligands in the regulation of blood vessel formation, the potential of VEGF-B as a therapeutic target for inhibition of tumor growth and metastasis is unclear. Although VEGF-B has been shown, along with other factors, to be expressed in a variety of tumors (Salven et al., *Am J Pathol,* 153:103-108, 1998), evidence of upregulation is limited (Li et al., *Growth Factors* 19:49-59, 2001) and there have been no reports of the efficacy of VEGF-B specific antagonists in xenograft or other relevant animal models. In fact, the potential of VEGF-B (and PLGF) is further confused by the disclosure by Cao et al in International PCT Publication No. WO03/62788, which suggests that increasing VEGF-B expression inhibits VEGF-A induced angiogenesis, and thus represents a potential approach to the treatment of diseases caused by VEGF-A activity and VEGF-A induced angiogenesis.

In accordance with the present invention, it has been surprisingly determined that antagonists of VEGF-B are useful in reducing the growth and development of cancer including tumor tissue.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO: 1), <400>2 (SEQ ID NO:2), etc. A summary of the sequence identifiers is provided in Table 1. A sequence listing is provided after the claims.

The present invention provides a method of inhibiting the growth of cancer including tumor tissue and pre-cancerous tissue using an antagonist of VEGF-B. Compositions are also provided comprising one or more VEGF-B antagonists alone or in combination with other anti-cancer agents or other angiogenesis-inhibiting agents.

An antagonist contemplated by the present invention may be an antibody which inhibits interaction between VEGF-B and VEGFR-1, an antisense compound which reduces VEGF-B expression, or an interfering nucleic acid which reduces VEGF-B expression.

The preferred antibodies bind to VEGF-B and interfere with VEGF-B interaction with its receptor. The antibody and other antagonists are proposed for use in treating certain conditions mediated in whole or in part, or directly or indirectly, by VEGF-B. The present invention also contemplates methods for treating these conditions in a subject comprising administering a VEGF-B antagonist.

In the case of antibodies or other antagonists directed towards human VEGF-B, some level of cross-reactivity with other mammalian forms of VEGF-B may be desirable in certain circumstances, such as for example, for the purpose of testing antibodies or other antagonists in animal models for their effect on a particular disease and for conducting toxicology studies in a manner where VEGF-B/VEGFR-1 receptor signaling in the test animal is affected by the test antibody or other antagonists. Species where cross-reactivity of an antibody or other antagonists to human VEGF-B may be desirable include mouse, dog and monkey. A particularly preferred group of antibodies of the present invention are those to human VEGF-B which exhibit cross-reactivity to murine VEGF-B.

In a related aspect, the antibodies of the present invention bind with the receptor binding domain (RBD) of VEGF-B and inhibit VEGF-B induced signaling through VEGFR-1. A particularly preferred group of antibodies of the present invention are those that bind with the human VEGF-B RBD and which also bind, interact, or otherwise associate to the murine VEGF-B RBD and inhibit VEGF-B induced signaling through the VEGFR-1.

Preferably, the antibodies are monoclonal antibodies ("mAbs") or antigen-binding fragments thereof. Even more preferably, the antibodies are humanized antibodies including deimmunized or chimeric antibodies or human antibodies suitable for administration to humans. Humanized antibodies, prepared, for example, from murine monoclonal antibodies and human monoclonal antibodies which are prepared, for example, using transgenic mice or by phage display are particularly preferred.

Antibodies in accordance with the present invention include the murine monoclonal antibodies 1C6, 2F5, 2H10 and 4E12, and humanized, deimmunized or chimeric forms of mAbs 1C6, 2F5, 2H10 and 4E12. The hybridoma cell line expressing the murine monoclonal anti-VEGF-B antibody 2H10 was deposited at the American Type Culture Collection (ATCC) on 27 Jul. 2005 under Accession No. PTA-6889.

The present invention contemplates methods of modulating VEGF-B-mediated diseases or conditions by the administration of VEGF-B antagonists, in particular antibodies of the present invention. Conditions to be treated in accordance with the present invention include cancers and tumors, and in particular solid tumors. Pre-cancerous conditions and dispersed tumors, such as for example, myelomas and lymphomas may also be treated.

A summary of sequence identifiers used throughout the subject specification is provided in

TABLE 1

Summary of sequence identifiers

| SEQUENCE ID NO: | DESCRIPTION |
|---|---|
| 1 | Amino acid sequence of the human VEGF-$B_{10-108}$ |
| 2 | Amino acid sequence of the murine VEGF-$B_{10-108}$ |
| 3 | Amino acid sequence of light chain variable region of the murine mAb 2H10 |

TABLE 1-continued

| Summary of sequence identifiers | |
|---|---|
| SEQUENCE ID NO: | DESCRIPTION |
| 4 | Amino acid sequence of heavy chain variable region of the murine mAb 2H10 |
| 5 | Amino acid sequence of 2H10 CDR-L1 |
| 6 | Amino acid sequence of 2H10 CDR-L2 |
| 7 | Amino acid sequence of 2H10 CDR-L3 |
| 8 | Amino acid sequence of 2H10 CDR-H1 |
| 9 | Amino acid sequence of 2H10 CDR-H2 |
| 10 | Amino acid sequence of 2H10 CDR-H3 |
| 11 | Amino acid sequence of light chain variable region of the murine mAb 4E12 |
| 12 | Amino acid sequence of heavy chain variable region of the murine mAb 4E12 |
| 13 | Amino acid sequence of 4E12 CDR-L1 |
| 14 | Amino acid sequence of 4E12 CDR-L2 |
| 15 | Amino acid sequence of 4E12 CDR-L3 |
| 16 | Amino acid sequence of 4E12 CDR-H1 |
| 17 | Amino acid sequence of 4E12 CDR-H2 |
| 18 | Amino acid sequence of 4E12 CDR-H3 |
| 19 | Amino acid sequence of light chain variable region of the murine mAb 2F5 |
| 20 | Amino acid sequence of heavy chain variable region of the murine mAb 2F5 |
| 21 | Amino acid sequence of 2F5 CDR-L1 |
| 22 | Amino acid sequence of 2F5 CDR-L2 |
| 23 | Amino acid sequence of 2F5 CDR-L3 |
| 24 | Amino acid sequence of 2F5 CDR-H1 |
| 25 | Amino acid sequence of 2F5 CDR-H2 |
| 26 | Amino acid sequence of 2F5 CDR-H3 |
| 27 | Amino acid sequence of the Human Variable Light Chain: Germline PK9/JK4 |
| 28 | Amino acid sequence of the Human Variable Heavy Chain: Germline DP75/JH4a |
| 29 | 2H10 CDR-Grafted Human Variable Light Chain: Germline PK9/JK4 |
| 30 | 2H10 CDR-Grafted Human Variable Heavy Chain: Germline DP75/JH4a |
| 31 | Nucleotide sequence of 2H10 CDR-L1 |
| 32 | Nucleotide sequence of 2H10 CDR-L1 optimised for expression in *E. coli* |
| 33 | Nucleotide sequence of 2H10 CDR-L2 |
| 34 | Nucleotide sequence of 2H10 CDR-L2 optimised for expression in *E. coli* |
| 35 | Nucleotide sequence of 2H10 CDR-L3 |
| 36 | Nucleotide sequence of 2H10 CDR-L3 optimised for expression in *E. coli* |
| 37 | Nucleotide sequence of 2H10 CDR-H1 |
| 38 | Nucleotide sequence of 2H10 CDR-H1 optimised for expression in *E. coli* |
| 39 | Nucleotide sequence of 2H10 CDR-H2 |
| 40 | Nucleotide sequence of 2H10 CDR-H2 optimised for expression in *E. coli* |
| 41 | Nucleotide sequence of 2H10 CDR-H3 |
| 42 | Nucleotide sequence of 2H10 CDR-H3 optimised for expression in *E. coli* |
| 43 | Amino acid sequence of light chain variable region of the murine mAb 1C6 |
| 44 | Amino acid sequence of heavy chain variable region of the murine mAb 1C6 |
| 45 | Amino acid sequence of 1C6 CDR-L1 |
| 46 | Amino acid sequence of 1C6 CDR-L2 |
| 47 | Amino acid sequence of 1C6 CDR-L3 |
| 48 | Amino acid sequence of 1C6 CDR-H1 |
| 49 | Amino acid sequence of 1C6 CDR-H2 |
| 50 | Amino acid sequence of 1C6 CDR-H3 |

A list of abbreviations used in the subject specification are shown in Table 2.

TABLE 2

| Abbreviations | |
|---|---|
| Abbreviation | Definition |
| VEGF | Vascular Endothelial Growth Factor |
| VEGF-B | Vascular Endothelial Growth Factor-B |
| VEGFR-1 | VEGF-B Receptor |
| PLGF | Placenta Growth Factor |
| Mabs | Monoclonal antibodies |
| 1C6 | Murine monoclonal antibody to VEGF-B |
| 2F5 | Murine monoclonal antibody to VEGF-B |
| 2H10 | Murine monoclonal antibody to VEGF-B |
| 4E12 | Murine monoclonal antibody to VEGF-B |
| RBD | Receptor Binding Domain |
| CDR | Complementarily Determining Regions |
| mVEGF-B | Murine VEGF-B |
| hVEGF-B | Human VEGF-B |
| $VEGF\text{-}B_{10\text{-}108}$ | Truncated form of VEGF-B comprising amino acids 10 through 108 |
| RT-PCR | Reverse Transcription-Polymerase Chain Reaction |

BRIEF DESCRIPTION OF THE FIGURES

FIG. 1 shows the heavy and light chain variable region amino acid sequences of anti-VEGF-B mAb 2H10. Amino acid numbering is according to Kabat et al., (Sequences of Proteins of Immunological Interest, 5th Ed. Public Health Service, National Institutes of Health, Bethesda, Md., 1991). CDR regions (underlined) are defined according to the sequence definition of Kabat et al. (supra), except for CDR-H1, which is the combined sequence and structural definition of Chothia and Lesk, *J. Mol. Biol.* 196:901-917, 1987.

FIG. 2 shows the heavy and light chain variable region amino acid sequences of anti-VEGF-B mAb 4E12. Amino acid numbering is according to Kabat et al., (supra). CDR regions (underlined) are defined according to the sequence definition of Kabat et al., (supra), except for CDR-H1, which is the combined sequence and structural definition of Chothia and Lesk (supra).

FIG. 3 shows the heavy and light chain variable region amino acid sequences of anti-VEGF-B mAb 2F5. Amino acid numbering is according to Kabat et al., (supra). CDR regions (underlined) are defined according to the sequence definition of Kabat et al. (supra), except for CDR-H1, which is the combined sequence and structural definition of Chothia and Lesk (supra).

FIG. 4 shows the Human Variable Light Chain Germline (PK9/JK4) amino acid sequence derived from the EmBL database sequences X93622 and J00242 (human unrearranged germline antibody light chain regions PK9 and JK4 respectively) and the Human Variable Heavy Chain Germline (DP75/JH4a) amino acid sequence derived from the EmBL database sequences HSIGDP75 and J00256 (human unrearranged germline antibody heavy chain regions DP75 and JH4a respectively). The CDR regions are underlined.

FIG. 5 shows the Human Variable Light Chain Germline (PK9/JK4) amino acid sequence and the Human Variable Heavy Chain Germline (DP75/JH4a) amino acid sequence following CDR-grafting with the CDR's of the murine anti-VEGF-B monoclonal antibody 2H10. The CDR regions are underlined. The amino acid at position 74 in the heavy chain sequence (Kabat numbering H73) was backmutated from Thr to Lys as described in Example 10.

FIG. 6 shows the nucleic acid sequences for the 2H10CDR regions optimised for expression in *E. coli.*

FIG. 7 shows the heavy and light chain variable region amino acid sequences of anti-VEGF-B mAb 1C6. Amino acid numbering is according to Kabat et al., (supra). CDR regions (underlined) are defined according to the sequence definition of Kabat et al. (supra), except for CDR-H1, which is the combined sequence and structural definition of Chothia and Lesk (supra).

DETAILED DESCRIPTION OF THE PREFERRED EMBODIMENTS

Before describing the present invention in detail, it is to be understood that unless otherwise indicated, the subject invention is not limited to specific formulations of components, manufacturing methods, dosage or diagnostic regimes, or the like. It is also to be understood that the terminology used herein is for the purpose of describing particular embodiments only, and is not intended to be limiting.

The singular forms "a", "an" and "the" include plural aspects unless the context clearly dictates otherwise. Thus, for example, reference to "an antibody" includes a single antibody, as well as two or more antibodies; reference to "a VEGF-B" includes a single VEGF-B as well as two or more VEGF-B molecules; reference to "an antagonist" includes a single antagonist as well as two or more antagonists; and so forth.

In describing and claiming the present invention, the following terminology is used in accordance with the definitions set forth below.

The terms "antagonist", "compound", "active agent", "pharmacologically active agent", "medicament" and "active" are used interchangeably herein to refer to a VEGF-B antagonist that induces a desired pharmacological and/or physiological effect. The terms also encompass pharmaceutically acceptable and pharmacologically active forms of those active agents specifically mentioned herein including but not limited to salts, esters, amides, prodrugs, active metabolites, analogs and the like. When the terms "antagonist", "compound", "active agent", "pharmacologically active agent", "medicament" and "active" are used, then it is to be understood that this includes the active agent per se as well as pharmaceutically acceptable, pharmacologically active salts, esters, amides, prodrugs, metabolites, analogs, etc.

Reference to an "antagonist", "compound", "active agent", "pharmacologically active agent", "medicament" and "active" may include combinations of two or more of such components, such as for example, two or more antibodies. A "combination" also includes multi-part combinations such as a two-part composition where the agents are provided separately and given or dispensed separately or admixed together prior to dispensation.

For example, a multi-part pharmaceutical pack may have two or more antibodies maintained separately or an anti-VEGF-B antibody and an anti-cancer agent or an angiogenesis-inhibiting agent.

The terms "effective amount" and "therapeutically effective amount" of an agent as used herein mean a sufficient amount of the VEGF-B antagonist to provide the desired therapeutic or physiological effect or outcome including inhibiting angiogenesis and/or inhibiting growth of cancer including tumor tissue. Undesirable effects, e.g. side effects, are sometimes manifested along with the desired therapeutic effect; hence, a practitioner balances the potential benefits against the potential risks in determining what is an appropriate "effective amount". The exact amount of agent required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation. The ability of a VEGF-B antagonist, preferably an antibody, to inhibit cancer can be evaluated in an animal model system predictive of efficacy in human tumors. One of ordinary skill in the art would be able to determine such amounts based on such factors as the subject's size, the severity of the subject's symptoms, and the particular composition or route of administration selected.

By "pharmaceutically acceptable" carrier and/or diluent is meant a pharmaceutical vehicle comprised of a material that is not biologically or otherwise undesirable, i.e. the material may be administered to a subject along with the selected active agent without causing any or a substantial adverse reaction. Carriers may include any and all solvents, dispersion media, coatings, antibacterial and antifungal agents, agents used for adjusting tonicity, buffers, chelating agents, and absorption delaying agents and the like.

Similarly, a "pharmacologically acceptable" salt, ester, amide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms of cancer, elimination of symptoms and/or underlying cause of cancer, prevention of the occurrence of symptoms of cancer and/or their underlying cause and improvement or remediation or amelioration of damage following a cancer.

The terms "cancer" and "tumor" may be used interchangeably and includes pre-cancerous condition.

"Treating" a subject may involve prevention of cancer growth or other adverse physiological event in a susceptible subject as well as treatment of a clinically symptomatic subject by ameliorating the symptoms of cancer.

A "subject" as used herein refers to an animal, preferably a mammal and more preferably a human who can benefit from the pharmaceutical formulations and methods of the present invention. There is no limitation on the type of animal that could benefit from the presently described pharmaceutical formulations and methods. A subject regardless of whether a human or non-human animal may be referred to as an individual, patient, animal, host or recipient as well as subject. The compounds and methods of the present invention have applications in human medicine and veterinary medicine.

Preferred animals are humans or laboratory test animals.

Examples of laboratory test animals include mice, rats, rabbits, guinea pigs, hamsters, cats and dogs.

The present invention employs conventional molecular biology, microbiology, and recombinant DNA techniques. The techniques are well known in the art and are described in various publications, such as Sambrook, Fritsch & Maniatis, Molecular Cloning: A Laboratory Manual, Second Edition, Cold Spring Harbor Laboratory Press, Cold Spring Harbor, N.Y., 1989.; DNA Cloning: A Practical Approach, Volumes I and II (D. N. Glover ed. 1985) and F. M. Ausubel, et al. (eds.), Current Protocols in Molecular Biology, John Wiley & Sons, Inc., 1994.

The terms "polynucleotide", "nucleic acid" or "nucleic acid molecule" refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine;

"DNA molecules"), or any phosphoester analogs thereof, such as phosphorothioates and thioesters, in single stranded form, double-stranded form or otherwise.

The terms "polynucleotide sequence", "nucleic acid sequence" or "nucleotide sequence" refer to a series of nucleotide bases (also referred to as "nucleotides") in a nucleic acid, such as DNA or RNA, and means any chain of two or more nucleotides.

The terms "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

The term "amplification" of nucleotide sequence as used herein may denote the use of the polymerase chain reaction (PCR) to increase the concentration of a particular nucleotide sequence within a mixture of nucleotide sequence sequences. Saiki, et al., *Science* 239: 487, 1988 provide a description of PCR. In a preferred embodiment, nucleic acids of the present invention include those which encode an anti-VEGF-B antibody, an anti-VEGF-B antibody heavy or light chain, an anti-VEGF-B antibody heavy or light chain variable region, an anti-VEGF-B antibody heavy or light chain constant region, an anti-VEGF-B antibody CDR (CDR-L1, CDR-L2, CDR-L3, CDR-H1, CDR-H2 or CDR-H3), a murine-human chimeric antibody as described herein, a CDR-Fab as described herein or humanized antibodies as described herein which can be amplified by PCR.

The term "oligonucleotide" refers to a nucleic acid, generally of at least 10, preferably at least 15, and more preferably at least 20 nucleotides, preferably no more than 100 nucleotides, that may be hybridizable to a genomic DNA molecule, a cDNA molecule, or an mRNA molecule encoding a gene, mRNA, cDNA, or other nucleic acid of interest. Oligonucleotides can be labelled for example, by incorporation of $32^P$-nucleotides, $3^H$-nucleotides, $14^C$-nucleotides, $35^S$-nucleotides or nucleotides to which a label, such as biotin, has been covalently conjugated. In one embodiment, a labelled oligonucleotide can be used as a probe to detect the presence of a nucleic acid. In another embodiment, oligonucleotides (one or both of which may be labelled) can be used as PCR primers, either for cloning full length or a fragment of the gene, or to detect the presence of nucleic acids. Generally, oligonucleotides are prepared synthetically, preferably on a nucleic acid synthesizer.

The sequence of any nucleic acid (for example, a nucleic acid encoding an VEGF-B gene or a nucleic acid encoding an anti-VEGF-B antibody or a fragment or portion thereof) may be sequenced by any method known in the art such as by chemical sequencing or enzymatic sequencing. "Chemical sequencing" of DNA may be done by the method of Maxam and Gilbert, (*Proc. Natl. Acad. Sci. USA* 74(2): 560-564, 1977), in which DNA is randomly cleaved using individual base-specific reactions. "Enzymatic sequencing" of DNA may be done by the method of Sanger (Sanger, et al., *Proc. Natl. Acad. Sci. USA* 74(12): 5463 5467, 1977).

Nucleic acids of the present invention may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

A "promoter" or "promoter sequence" is a DNA regulatory region capable of binding an RNA polymerase in a cell and initiating transcription of a coding sequence. A promoter sequence is generally bounded at its 3' terminus by the transcription initiation site and extends upstream in the 5' direction to include the minimum number of bases or elements necessary to initiate transcription at any level. A transcription initiation site as well as protein binding domains (consensus sequences) responsible for the binding of RNA polymerase may be found within the promoter sequence. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062) and the SV40 early promoter region (Benoist, et. al., *Nature* 290:304-310, 1981).

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be trans-RNA spliced (if it contains introns) and, optionally, translated into a protein encoded by the coding sequence.

The terms "express" and "expression" mean allowing or causing the information in a gene, RNA or DNA sequence to be converted into a product; for example, producing a protein by activating the cellular functions involved in transcription and translation of a nucleotide sequence. A DNA sequence is expressed in or by a cell to form an "expression product" such as RNA (such as mRNA) or a protein (such as the anti-VEGF-B antibody). The expression product itself may also be said to be "expressed" by the cell.

The terms "vector", "cloning vector" and "expression vector" mean the vehicle (such as a plasmid) by which a DNA or RNA sequence can be introduced into a host cell, so as to transform the host and, optionally, promote expression and/or replication of the introduced sequence.

The term "transfection" or "transformation" means the introduction of a nucleic acid into a cell. These terms may refer to the introduction of a nucleic acid encoding an anti-VEGF-B antibody or fragment thereof into a cell. The introduced gene or sequence may be called a "clone". A host cell that receives the introduced DNA or RNA has been "transformed" and is a "transformant" or a "clone". The DNA or RNA introduced to a host cell can come from any source, including cells of the same genus or species as the host cell, or cells of a different genus or species.

The term "host cell" means any cell of any organism that is selected, modified, transfected, transformed, grown, or used or manipulated in any way, for the production of a substance by the cell, for example the expression or replication, by the cell, of a gene, a DNA or RNA sequence, a protein or an enzyme.

The term "expression system" means a host cell and compatible vector which, under suitable conditions, can express a protein or nucleic acid which is carried by the vector and introduced to the host cell. Common expression systems include *E. coli* host cells and plasmid vectors, insect host cells and Baculovirus vectors, and mammalian host cells and vectors.

The present invention relates generally to a method of inhibiting the growth of cancers including tumorous tissue as well as pre-cancerous tissue by inhibiting the signalling function of VEGF-B. This may occur by inhibiting VEGF-B activity, inhibiting VEGF-B interaction with a receptor or reducing VEGF-B expression. Accordingly, the present invention contemplates a method for the treatment of cancer and compositions and agents useful for same. In a preferred embodiment, the present invention provides antibodies which antagonize VEGF-B/VEGFR-1 interaction.

However, the present invention extends to other VEGF-B antagonists including an antisense compound which reduces VEGF-B expression, or an interfering nucleic acid which reduces VEGF-B expression. An interfering nucleic acid molecule includes synthetic or DNA-derived RNAi.

VEGF-B antagonists may be prepared by a range of methods. For example, nucleic acid-based compounds may be prepared using the general approaches taught in US Patent Application 20040102389 and include, enzymatic nucleic acid molecules (ribozymes such as Inozyme, G-cleaver, amberzyme, zinzyme), DNAzymes, 2-5A antisense chimeras, triplex forming nucleic acid, decoy nucleic acids, aptamers, allozymes, antisense nucleic acids containing RNA cleaving chemical groups (Cook et al., U.S. Pat. No. 5,359,051), small interfering nucleic acid (siRNA, Beigelman et al., U.S. Ser. No. 60/409,293).

Antisense compounds which reduce VEGF-B expression are described in Zhang and Dobie, International PCT Publication No. WO03/105754. Interfering nucleic acid molecules, such as short interfering nucleic acid (siRNA), short interfering RNA (siRNA), double-stranded RNA (dsRNA), micro-RNA (miRNA), and short hairpin RNA (shRNA) molecules capable of mediating RNA interference (RNAi) against VEGF-B and/or which reduce VEGF-B expression may be prepared using the general approach described in McSwiggen et al., International PCT Publication No. WO 03/070910.

The preferred antagonists of the present invention are directed towards human VEGF-B. However, cross-reactive VEGF-B antagonists, i.e. that antagonize human and other mammalian forms of VEGF-B may be desirable and form another aspect of the present invention.

The antibodies preferably are monoclonal antibodies. Preferably, the antibodies are in isolated, homogenous or fully or partially purified form.

Most preferably, the antibodies are humanized or chimeric or are human antibodies suitable for administration to humans. These include humanized antibodies prepared, for example, from murine monoclonal antibodies, and human monoclonal antibodies which may be prepared, for example, using transgenic mice as described below, or by phage display. A "humanized" antibody includes a deimmunized antibody.

Reference to "VEGF-B" includes all naturally occurring isoforms of VEGF-B, including VEGF-$B_{167}$ and VEGF-$B_{186}$ (Olofsson et al., *J Biol. Chem.* 271:19310-19317, 1996), naturally occurring processed forms of VEGF-B, together with any genetically engineered forms based on the sequence of the naturally occurring VEGF-B proteins. VEGF-B is a member of the VEGF family of growth factors, and like all members of this family incorporates a VEGF homology domain (Olofsson et al., *Curr Opin in Biotech. Vol* 10:528-535, 1999). The homology domain is characterised by a structural motif referred to as a cystine-knot, and it is this part of the protein that retains peptides sequences principally responsible for binding with VEGFR-1. For human and murine VEGF-B, the VEGF homology domain is contained within a genetically engineered form that spans amino acids 10-108 of the mature forms of both VEGF-$B_{167}$ and VEGF-$B_{186}$. The VEGF homology domain of VEGF-B can also be referred to as the receptor binding domain (RBD). Engineered VEGF-$B_{10-108}$ binds to the ligand binding domain of VEGFR-1, and shows activity in a chimeric receptor assay designed to demonstrate signalling through VEGFR-1 (Scotney et al., *Clin Exp Pharmacol Physiol* (*Australia*), 29(11): 1024-9, 2002).

VEGF-B molecules in accordance with the present invention include human VEGF-$B_{167}$ (NCBI Accession Number AAB06274; protein sequence includes the signal sequence), human VEGF-$B_{186}$ (NCBI Accession Number AAC50721; protein sequence includes the signal sequence), murine VEGF-$B_{167}$ (NCBI Accession Number AAB06273; protein sequence includes the signal sequence), murine VEGF-$B_{186}$ (NCBI Accession Number AAC52823; protein sequence includes the signal sequence) and engineered forms thereof referred to as human VEGF-$B_{10-108}$ (SEQ ID NO:1) and murine VEGF-$B_{10-108}$ (SEQ ID NO:2).

The sequence of human VEGF-$B_{10-108}$ corresponds to the sequence of amino acids from amino acid 31 (H) to amino acid 129 (K) inclusive of the human VEGF-$B_{167}$ protein sequence shown in NCBI Accession Number AAB06274, and to the sequence of amino acids from amino acid 31 (H) to amino acid 129 (K) inclusive of the human VEGF-$B_{186}$ protein sequence shown in NCBI Accession Number AAC50721.

The sequence of murine VEGF-$B_{10-108}$ corresponds to the sequence of amino acids from amino acid 31 (H) to amino acid 129 (K) inclusive of the murine VEGF-$B_{167}$ protein sequence shown in NCBI Accession Number AAB06273 and to the sequence of amino acids from amino acid 31 (H) to amino acid 129 (K) inclusive of the murine VEGF-$B_{186}$ protein sequence shown in NCBI Accession Number AAC52823.

Examples of antibodies contemplated by the present invention include those that bind to VEGF-B and block the signaling of VEGF-B through VEGFR-1, thereby inhibiting a VEGF-B-induced biological activity. Such antibodies may be raised against a VEGF-B polypeptide or an antigenic part thereof or an immunogenic part, such as for example, VEGF-$B_{167}$ or peptides containing the receptor binding domain (RBD) such as VEGF-$B_{10-108}$. Antibodies that have the ability to block the signaling of VEGF-B through VEGFR-1 may be selected using cell based or biochemical assays, such as, but not limited to those assays described herein. Preferably, antibodies are raised against a human VEGF-B polypeptide or immunogenic parts thereof. Preferably, antibodies which block human VEGF-B signaling are selected.

Preferred antibodies of the present invention are antibodies that bind to human VEGF-B and inhibit human VEGF-B induced signaling through VEGFR-1.

In a further preferred embodiment, the present invention provides antibodies that bind to human VEGF-$B_{10-108}$ (SEQ ID NO:1) and inhibit VEGF-B induced signaling through VEGFR-1.

In an even further preferred embodiment, the present invention provides antibodies that bind to the human VEGF-B RBD and inhibit VEGF-B induced signaling through VEGFR-1.

In the case of antibodies directed towards human VEGF-B, some level of cross-reactivity with other mammalian forms of VEGF-B may be desirable in certain circumstances, such as for example, for the purpose of testing antibodies in animal models for their affect on a particular disease and for conducting toxicology studies in a manner where VEGF-B/VEGFR-1 signaling in the test animal is affected by the test antibody. Species where cross-reactivity of an antibody to human VEGF-B may be desirable include mouse, rat, dogs and monkey. A particularly preferred group of antibodies of the present invention are those to human VEGF-B which exhibit some level of species cross-reactivity to murine VEGF-B ("mVEGF-B"). Cross-reactivity means that an antibody binds with high affinity to human VEGF-B and VEGF-B from the other species, and inhibits interaction of VEGF-B with VEGFR-1. Cross-reactivity for other VEGF-B antagonists, such as antisense or interfering RNA's, means that they may reduce expression of human VEGF-B and VEGF-B from the other species.

Preferred antibodies of the present invention and for use in the methods of the present invention are antibodies that are cross-reactive with VEGF-B from two or more species and inhibit VEGF-B induced signaling through VEGFR-1.

Particularly preferred antibodies of the present invention are antibodies that bind to human VEGF-B and to murine VEGF-B and inhibit VEGF-B induced signaling through VEGFR-1.

In a preferred embodiment, the present invention provides antibodies that bind to human VEGF-$B_{10-108}$ (SEQ ID NO:1) and to murine VEGF-$B_{10-108}$ (SEQ ID NO:2) and inhibit VEGF-B induced signaling through VEGFR-1.

In a further preferred embodiment, the present invention provides antibodies that bind to the human VEGF-B RBD and to the murine VEGF-B RBD and inhibit VEGF-B induced signaling through VEGFR-1.

Preferably, the antibodies are monoclonal antibodies.

Most preferably, the antibodies are human or humanized including deimmunized monoclonal antibodies suitable for use in human therapeutics.

In one embodiment, the present invention provides antibodies that are human or humanized monoclonal antibodies that bind to VEGF-B and block the signaling of VEGF-B through VEGFR-1.

In a preferred embodiment, the present invention provides antibodies that are human or humanized monoclonal antibodies that bind to human VEGF-B and inhibit human VEGF-B induced signaling through VEGFR-1.

In a further preferred embodiment, the present invention provides antibodies that are human or humanized monoclonal antibodies that bind to human VEGF-$B_{10-108}$ (SEQ ID NO: 1) and inhibit VEGF-B induced signaling through VEGFR-1.

In an even further preferred embodiment, the present invention provides antibodies that are human or humanized monoclonal antibodies that bind to the human VEGF-B RBD and inhibit VEGF-B induced signaling through VEGFR-1.

In another preferred embodiment, the present invention provides antibodies that are human or humanized monoclonal antibodies that are cross-reactive with VEGF-B from two or more species and inhibit VEGF-B induced signaling through VEGFR-1.

In a preferred embodiment, the present invention provides antibodies that are human or humanized monoclonal antibodies that bind to human VEGF-B and to murine VEGF-B and inhibit VEGF-B signaling through VEGFR-1.

In a further preferred embodiment, the present invention provides antibodies that are human or humanized monoclonal antibodies that bind to human VEGF-$B_{10-108}$ (SEQ ID NO:1) and which also bind to murine VEGF-$B_{10-108}$ (SEQ ID NO:2) and inhibit VEGF-B signaling through VEGFR-1.

In an especially preferred embodiment, the present invention provides antibodies that are human or humanized monoclonal antibodies that bind to the hVEGF-B RBD and which also bind to the mVEGF-B RBD and inhibit VEGF-B signaling through VEGFR-1.

The present invention also contemplates anti-VEGF-B antibodies which compete with the antibodies of the present invention, and in a particularly preferred embodiment, the 2H10 monoclonal antibody produced by the hybridoma cell line deposited with ATCC on 27 Jul. 2005 under Accession No. PTA-6889, for binding to VEGF-B as well as antigen-binding fragments of the competing antibodies, and human or humanized forms of the competing antibodies or their antigen-binding fragments.

In a further preferred embodiment, the competing antibodies have CDRs which are the same as the CDRs of the monoclonal antibody 2H10. Examples of antibodies that compete with the monoclonal antibody 2H10 for binding to VEGF-B include 1C6 and 2F5.

Reference to an "antibody" or "antibodies" includes reference to all the various forms of antibodies, including but not limited to: full antibodies (e.g. having an intact Fc region), including, for example, monoclonal antibodies; antigen-binding fragments of antibodies including, for example, Fv, Fab, Fab' and $F(ab')_2$ fragments; humanized antibodies; human antibodies (e.g., produced in transgenic animals or through phage display); and immunoglobulin-derived polypeptides produced through genetic engineering techniques. Unless otherwise specified, the terms "antibody" or "antibodies" and as used herein encompasses both full antibodies and antigen-binding fragments thereof.

Unless slated otherwise, specificity in respect of an antibody of the present invention is intended to mean that the antibody binds substantially only to its target antigen with no appreciable binding to unrelated proteins. However, it is possible that an antibody will be designed or selected to bind to two or more related proteins. A related protein includes different splice variants or fragments of the same protein or homologous proteins from different species. Such antibodies are still considered to have specificity for those proteins and are encompassed by the present invention. The term "substantially" means in this context that there is no detectable binding to a non-target antigen above basal, i.e. non-specific, levels.

Antibodies which bind VEGF-B are referred to as anti-VEGF-B antibodies.

The antibodies of the present invention may be prepared by well known procedures. See, for example, Monoclonal Antibodies, Hybridomas: A New Dimension in Biological Analyses, Kennet et al. (eds.), Plenum Press, New York (1980); and Antibodies: A Laboratory Manual, Harlow and Lane (eds.), Cold Spring Harbor Laboratory Press, Cold Spring Harbor, N.Y., (1988).

One method for producing an antibody of the present invention comprises immunizing a non-human animal, such as a mouse or a transgenic mouse, with a VEGF-B polypeptide, or immunogenic parts thereof, such as, for example, a peptide containing the RBD, whereby antibodies directed against the VEGF-B polypeptide or immunogenic parts are generated in said animal. Various means of increasing the antigenicity of a particular immunogen, such as administering adjuvants or conjugated antigens, comprising the antigen against which an antibody response is desired and another component, are well known to those in the art and may be utilized. Immunizations typically involve an initial immunization followed by a series of booster immunizations. Animals may be bled and the serum assayed for antibody titer. Animals may be boosted until the titer plateaus. Conjugates may be made in recombinant cell culture as protein fusions. Also, aggregating agents such as alum are suitably used to enhance the immune response.

Both polyclonal and monoclonal antibodies can be produced by this method. The methods for obtaining both types of antibodies are well known in the art. Polyclonal antibodies are less preferred but are relatively easily prepared by injection of a suitable laboratory animal with an effective amount of a VEGF-B polypeptide, or immunogenic parts thereof, collecting serum from the animal and isolating VEGF-B specific antibodies by any of the known immunoadsorbent techniques. Antibodies produced by this technique are generally less favoured, because of the potential for heterogeneity of the product.

The use of monoclonal antibodies is particularly preferred because of the ability to produce them in large quantities and the homogeneity of the product. Monoclonal antibodies may be produced by conventional procedures.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using for example, the techniques described in Clackson et al., *Nature* 352:624-628, 1991 and Marks et al., *J. Mol. Biol.* 222:581-597, 1991.

The present invention contemplates a method for producing a hybridoma cell line which comprises immunizing a non-human animal, such as a mouse or a transgenic mouse, with a VEGF-B polypeptide, such as, for example, human VEGF-$B_{167}$, or immunogenic parts thereof, such as, for example, a peptide containing the RBD, such as VEGF-$B_{10-108}$ (SEQ ID NO:1) and (SEQ ID NO:2); harvesting spleen cells from the immunized animal; fusing the harvested spleen cells to a myeloma cell line to generate hybridoma cells; and identifying a hybridoma cell line that produces a monoclonal antibody that binds a VEGF-B polypeptide.

Such hybridoma cell lines and the anti-VEGF-B monoclonal antibodies produced by them are encompassed by the present invention. Monoclonal antibodies secreted by the hybridoma cell lines are purified by conventional techniques. Hybridomas or the monoclonal antibodies produced by them may be screened further to identify monoclonal antibodies with particularly desirable properties, such as the ability to inhibit VEGF-B-signaling through VEGFR-1.

The VEGF-B polypeptide or immunogenic part thereof that may be used to immunize animals in the initial stages of the production of the antibodies of the present invention may be from any mammalian source. Preferably, the VEGF-B polypeptide or immunogenic part thereof is human VEGF-B and includes the RBD region.

Antigen-binding fragments of antibodies of the present invention may be produced by conventional techniques. Examples of such fragments include, but are not limited to, Fab, Fab', $F(ab')_2$ and Fv fragments, including single chain Fv fragments (termed sFv or scFv). Antibody fragments and derivatives produced by genetic engineering techniques, such as disulphide stabilized Fv fragments (dsFv), single chain variable region domain (Abs) molecules, minibodies and diabodies are also contemplated for use in accordance with the present invention.

Such fragments and derivatives of monoclonal antibodies directed against VEGF-B may be prepared and screened for desired properties, by known techniques, including the assays described herein. The assays described herein provide the means to identify fragments and derivatives of the antibodies of the present invention that bind to VEGF-B, as well as identify those fragments and derivatives that also retain the activity of inhibiting signaling by VEGF-B through VEGFR-1. Certain of the techniques involve isolating DNA encoding a polypeptide chain (or a portion thereof) of a mAb of interest, and manipulating the DNA through recombinant DNA technology. The DNA may be fused to another DNA of interest, or altered (e.g. by mutagenesis or other conventional techniques) to add, delete, or substitute one or more amino acid residues, for example.

DNA encoding antibody polypeptides (e.g. heavy or light chain, variable region only or full length) may be isolated from B-cells of mice that have been immunized with VEGF-B. The DNA may be isolated using conventional procedures.

The present invention contemplates any slight modifications of the amino acid or nucleotide sequences which correspond to the antibodies, antigen-binding fragments or humanized forms of the invention. In particular, the present invention contemplates sequence conservative variants of the nucleic acids which encode the antibodies or antigen-binding fragments of the invention. "Sequence-conservative variants" of a polynucleotide sequence are those in which a change of one or more nucleotides in a given codon results in no alteration in the amino acid encoded at that position. (FIG. 6) Function-conservative variants of the antibodies of the invention are also contemplated by the present invention. "Function-conservative variants" are those in which one or more amino acid residues in a protein have been changed without altering the overall conformation and function of the protein, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

The present invention includes anti-VEGF-B antibodies and fragments thereof which are encoded by nucleic acids as described herein as well as nucleic acids which hybridize thereto. Preferably, the nucleic acids hybridize under low stringency conditions, more preferably under moderate stringency conditions and most preferably under high stringency conditions and, preferably, exhibit VEGF-B binding activity. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions may be 55° C., 5 times SSC, 0.1% SDS, 0.25% milk, and no formamide; or 30% formamide, 5 times SSC and 0.5% SDS. Typical moderate stringency hybridization conditions are similar to the low stringency conditions except the hybridization is carried out in 40% formamide, with 5 or 6 times SSC. High stringency hybridization conditions are similar to low stringency conditions except the hybridization conditions are carried out in 50% formamide, 5 or 6 times SSC and, optionally, at a higher temperature (e.g., 57 to 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al. supra). For hybridization with shorter nucleic acids, i.e., oligonucleotides, the position of mismatches becomes more important, and the length of the oligonucleotide determines its specificity (see Sambrook, et al. supra).

Also included in the present invention are nucleic acids comprising nucleotide sequences and polypeptides comprising amino acid sequences which are at least about 70% identical, preferably at least about 80% identical, more preferably at least about 90% identical and most preferably at least about 95% identical to the nucleotide and amino acid sequences described herein when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the amino acid sequences described herein when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity refers to both exact matches between the amino acids of two polypeptides which are being compared in addition to matches between non-identical, biochemically related amino acids. Biochemically related amino acids which share similar properties and may be interchangeable are discussed above.

Descriptions for BLAST algorithms can be found in the following references which herein incorporated by reference: BLAST ALGORITHMS: Altschul, S. F., et al., *J. Mol. Biol.* 215:403-410, 1990; and Altschul, S. F., et al., *Nucleic Acids Res.* 25:3389-3402, 1997; Altschul, S. F., *J. Mol. Biol.* 219: 555-565, 1991.

The anti-VEGF-B antibody molecules of the present invention may also be produced recombinantly (for example, in an *E. coli* expression system). There are several methods by which to produce recombinant antibodies which are known in the art. One example of a method for recombinant production of antibodies is disclosed in U.S. Pat. No. 4,816,567 which is herein incorporated by reference. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

In one aspect, the present invention provides a method for the production of the antibodies of the present invention, said method comprising cloning nucleic acid sequences encoding the antibodies of the present invention into an appropriate vector, transforming a host cell line with the vector, and culturing the transformed host cell line under conditions suitable for the expression of the antibodies of the present invention.

Vectors available for cloning and expression in host cell lines are well known in the art, and include but are not limited to vectors for cloning and expression in mammalian cell lines, vectors for cloning and expression in bacterial cell lines and vectors for cloning and expression insect cell lines. The antibodies can be recovered using standard protein purification methods.

In another aspect, the present invention provides nucleic acid sequences encoding antibodies comprising CDRs having the sequences shown in SEQ ID NOs: 5 to 10, or SEQ ID NOs: 13 to 18, or SEQ ID NOs: 21 to 26, or SEQ ID NOs: 45 to 50 or antibodies comprising the variable light chain and the variable heavy chain sequences shown in SEQ. ID NOs: 3 and 4, or SEQ ID NOs: 11 and 12, or SEQ ID NOs: 19 and 20, or SEQ ID NOs: 43 and 44, or SEQ ID NOs: 29 and 30.

In a further aspect, the present invention provides vectors comprising nucleic acid sequences encoding antibodies comprising CDRs having the sequences shown in SEQ ID NOs: 5 to 10, or SEQ ID NOs: 13 to 18, or SEQ ID NOs: 21 to 26, or SEQ ID NOs: 45 to 50.

In still a further aspect, the present invention provides vectors comprising nucleic acid sequences encoding antibodies comprising the variable light chain sequences and the variable heavy chain sequences shown in SEQ ID NOs: 3 and 4, or SEQ ID NOs: 11 and 12, or SEQ ID NOs: 19 and 20, or SEQ ID NOs: 43 and 44, or SEQ ID NOs: 29 and 30.

In a preferred aspect, the present invention provides vectors comprising nucleic acid sequences encoding antibodies comprising the variable light chain sequences and the variable heavy chain sequences shown in SEQ ID NOs: 29 and 30.

In still a further aspect, the present invention provides host cell lines transformed with the vectors of the present invention.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9. cells, amphibian cells, bacterial cells, plant cells and fungal cells. When recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

Single chain antibodies may be formed by linking heavy and light chain variable region (Fv region) fragments via an amino acid bridge (short peptide linker), resulting in a single polypeptide chain. Such single-chain Fvs (scFvs) have been prepared by fusing DNA encoding a peptide linker between DNAs encoding the two variable region polypeptides (VL and VH). The resulting antibody fragments can form dimers or trimers, depending on, the length of a flexible linker between the two variable domains (Kortt et al., *Protein Engineering* 10: 423, 1997). Techniques developed for the production of single chain antibodies include those described in U.S. Pat. No. 4,946,778; Bird (*Science* 242: 423, 1988), Huston et al. (*Proc. Natl. Acad. Sci. USA* 85: 5879, 1988) and Ward et al. (*Nature* 334: 544, 1989). Single chain antibodies derived from antibodies provided herein are encompassed by the present invention.

In one embodiment, the present invention provides antibody fragments or chimeric, recombinant or synthetic forms of the antibodies of the present invention that bind to VEGF-B from two or more animal species, and inhibit signaling by VEGF-B through VEGFR-1.

Techniques are known for deriving an antibody of a different subclass or isotype from an antibody of interest, i.e., subclass switching. Thus, IgG1 or IgG4 monoclonal antibodies may be derived from an IgM monoclonal antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g. DNA encoding the constant region of an antibody of the desired isotype.

The monoclonal production process described above may be used in animals, for example mice, to produce monoclonal antibodies. Conventional antibodies derived from such animals, for example murine antibodies, are known to be generally unsuitable for administration to humans as they may cause an immune response. Therefore, such antibodies may need to be modified in order to provide antibodies suitable for administration to humans. Processes for preparing chimeric and/or humanized antibodies are well known in the art and are described in further detail below.

The monoclonal antibodies herein specifically include "chimeric" antibodies in which the variable domain of the heavy and/or light chain is identical with or homologous to corresponding sequences in antibodies derived from a non-human species (e.g., murine), while the remainder of the chain(s) is identical with or homologous to corresponding sequences in antibodies derived from humans, as well as fragments of such antibodies, so long as they exhibit the desired biological activity (U.S. Pat. No. 4,816,567; and Morrison et al., *Proc. Natl. Acad. Sci. USA* 81:6851-6855, 1984).

"Humanized" forms of non-human (e.g., murine) antibodies are chimeric antibodies which contain minimal sequence derived from the non-human immunoglobulin. For the most part, humanized antibodies are human immunoglobulins (recipient antibody) in which the complementarity determining regions (CDRs) of the recipient are replaced by the corresponding CDRs from a non-human species (donor antibody) such as mouse, rat, rabbit or nonhuman primate having the desired properties, for example specificity, and affinity. In some instances, framework region residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the complementarity determining regions correspond to those of a non-human immunoglobulin and all or substantially all of the framework region residues are those of a human immunoglobulin sequence. The humanized antibody optionally also will comprise at least a portion of an immunoglobulin constant region (Fc), typically that of a human immunoglobulin. For further details, see Jones et al., *Nature* 321:522-525, 1986; Reichmann et al., *Nature* 332:323-329, 1988; Presta, *Curr. Op. Struct. Biol.* 2:593-596, 1992; Liu et al., *Proc. Natl. Acad. Sci. USA* 84: 3439, 1987; Larrick et al., *Bio/Technology* 7: 934, 1989; and Winter and Harris, *TIPS* 14: 139, 1993.

The complementarity determining regions (CDRs) of a given antibody may be readily identified, for example using the system described by Kabat et al. in Sequences of Proteins of Immunological Interest, 5th Ed., US Dept. of Health and Human Services, PHS, NIH, NIH Publication No. 91-3242, 1991).

For example, the murine monoclonal antibodies 1C6, 2F5, 2H10 and 4E12 can be humanized to reduce the immunogenicity of the antibodies in a target host. Murine monoclonal antibodies 1C6, 2F5, 2H10 and 4E12 have antagonistic effect against VEGF-B and inhibit signaling through VEGFR-1. However, the potential immunogenicity of the mAbs 1C6, 2F5, 2H10 and 4E12 in other hosts, and in particular humans, makes the use of mAbs 1C6, 2F5, 2H10 and 4E12 unsuitable as therapeutic agents in these hosts.

In a particular embodiment, antibodies of the present invention comprise within the variable region of their light chain, at least one of the CDRs found in the light chain of mAb 2H10. The CDRs of mAb 2H10 are disclosed in FIG. 1 and in SEQ ID NOs: 5-10. Thus, among the antibodies contemplated by the present invention are those that comprise from one to all three of the CDR sequences from the light chain variable region of mAb 2H10. Further, among the antibodies contemplated by the present invention are those that comprise from one to all three of the CDR sequences from the heavy chain variable region of mAb 2H10. In a preferred embodiment, antibodies of the present invention comprise one, two, three, four, five or all six CDR sequences from the heavy and light chain variable regions of mAb 2H10.

In a particular embodiment, antibodies of the present invention comprise within the variable region of their light chain, at least one of the CDRs found in the light chain of mAb 4E12. The CDRs of mAb 4E12 are disclosed in FIG. 2 and in SEQ ID NOs: 13-18. Thus, among the antibodies contemplated by the present invention are those that comprise from one to all three of the CDR sequences from the light chain variable region of mAb 4E 12. Further, among the antibodies contemplated by the present invention are those that comprise from one to all three of the CDR sequences from the heavy chain variable region of mAb 4E12. In a preferred embodiment, antibodies of the present invention comprise one, two, three, four, five or all six CDR sequences from the heavy and light chain variable regions of mAb 4E12.

In a particular embodiment, antibodies of the present invention comprise within the variable region of their light chain, at least one of the CDRs found in the light chain of mAb 2F5. The CDRs of mAb 2F5 are disclosed in FIG. 3 and in SEQ ID NOs: 21-26. Thus, among the antibodies contemplated by the present invention are those that comprise from one to all three of the CDR sequences from the light chain variable region of mAb 2F5. Further, among the antibodies contemplated by the present invention are those that comprise from one to all three of the CDR sequences from the heavy chain variable region of mAb 2F5. In a preferred embodiment, antibodies of the present invention comprise one, two, three, four, five or all six CDR sequences from the heavy and light chain variable regions of mAb 2F5.

In a particular embodiment, antibodies of the present invention comprise within the variable region of their light chain, at least one of the CDRs found in the light chain of mAb 1C6. The CDRs of mAb 2H10 are disclosed in FIG. 7 and in SEQ ID NOs: 45-50. Thus, among the antibodies contemplated by the present invention are those that comprise from one to all three of the CDR sequences from the light chain variable region of mAb 1C6. Further, among the antibodies contemplated by the present invention are those that comprise from one to all three of the CDR sequences from the heavy chain variable region of mAb 1C6. In a preferred embodiment, antibodies of the present invention comprise one, two, three, four, five or all six CDR sequences from the heavy and light chain variable regions of mAb 1C6.

Procedures for generating human antibodies in non-human animals have been developed and are well known to those skilled in the art. For example, transgenic mice into which genetic material encoding one or more human immunoglobulin chains has been introduced may be used to produce the antibodies of the present invention. Antibodies produced in the animals incorporate human immunoglobulin polypeptide chains encoded by the human genetic material introduced into the animal. Examples of techniques for production and use of such transgenic animals are described in U.S. Pat. Nos. 5,814,318, 5,569,825, and 5,545,806, which are incorporated by reference herein.

Another method for generating human antibodies is phage display. Phage display techniques for generating human antibodies are well known to those skilled in the art, and include the methods used by companies such as Cambridge Antibody Technology and MorphoSys and which are described in International Patent Publication Nos. WO 92/01047, WO 92/20791, WO 93/06213 and WO 93/11236.

Antibodies of the present invention may be employed in vitro or in vivo to inhibit a biological activity that results from VEGF-B signaling. Among other uses for the antibodies of the present invention are assays (either in vitro or in vivo) to detect the presence of VEGF-B polypeptides and immunoaffinity chromatography to purify VEGF-B polypeptides.

Therefore, in one embodiment, antibodies of the present invention may be used in therapeutic applications to treat diseases or conditions caused or exacerbated (directly or indirectly) by the signaling of VEGF-B through the VEGF-B receptor. A therapeutic application involves in vivo administration of an antibody of the present invention to a mammal in an amount effective to inhibit signaling by VEGF-B through VEGFR-1. Preferably, the antibodies are human or humanized monoclonal antibodies of the present invention.

The antibodies may be used to treat diseases or conditions induced by VEGF-B including but not limited to cancer, in particular tumors, more particularly solid tumors.

Antibodies in accordance with the present invention are the murine monoclonal antibodies 1C6, 2H10, 4E12 and 2F5, and humanized forms of mAbs 1C6, 2F5, 2H10 and 4E12.

Antibodies of the present invention also include, but are not limited to monoclonal antibodies directed against amino acid residues 10 to 108 of the human VEGF-B (SEQ ID NO: 1) and/or amino acid residues 10 to 108 of the murine VEGF-B (SEQ ID NO:2) and which bind to VEGF-B from two or more animal species.

Particular monoclonal antibodies of the invention are selected from the group consisting of the mAbs 1C6, 2H10, 4E12 and 2F5; mAbs that bind to the same epitope as the mAbs 1C6, 2H10, 4E12 and 2F5; a mAb that competes with the mAbs 1C6, 2H10, 4E12 or 2F5 for binding to human VEGF-B; a mAb that competes with the mAbs 1C6, 2H10, 4E12 or 2F5 for binding to human VEGF-$B_{10-108}$; a mAb that possesses a biological activity of the mAbs 1C6, 2H10, 4E12 or 2F5; and an antigen-binding fragment of any of the foregoing antibodies that inhibits binding of VEGF-B or VEGF-$B_{10-108}$ to VEGFR-1. Antibodies in accordance with this embodiment include 1C6, 2H10, 4E12 and 2F5 and humanized forms thereof as discussed in the Examples.

In one embodiment, the antibody has a binding affinity for human VEGF-B or VEGF-$B_{10-108}$ that is substantially equivalent to the binding affinity of a mAb selected from 1C6, 2H10, 4E12 and 2F5 for human VEGF-B or VEGF-$B_{10-108}$. mAbs of any isotype (including but not limited to IgG4, $IgG_1$), derived from mAbs 1C6, 2H10, 4E12 and 2F5 are also encompassed by the present invention. Hybridoma cell lines that produce any such monoclonal antibodies also are provided by the present invention.

Antibody affinities may be determined using a biosensor-based approach as described in the examples section. Preferred antibodies are those which bind human VEGF-B with a $K_D$ value of $1\times10^{-7}$ M or less; preferably $1\times10^{-8}$ M or less; more preferably $1\times10^{-9}$ M or less; and most preferably $5\times10^{-10}$ M or less as determined by surface plasmon resonance. One example of a biological activity of a mAb selected from 1C6, 2H10, 4E12 and 2F5 is its ability to bind to VEGF-B and inhibit signaling by VEGF-B through VEGFR-1. In one embodiment, a mAb of the invention possesses biological activity or VEGF-B blocking activity substantially equivalent to that of a mAb selected from 1C6, 2H10, 4E12 and 2F5. Such activity may be measured in any suitable assay (e.g. as measured in the VEGFR-1/EpoR/BaF3 proliferation assay described herein or in a reporter gene assay such as that described by Scotney et al. (supra).

In one assay, Ba/F3 cells are transfected with a chimeric receptor incorporating the intracellular domain of the erythropoietin receptor (EpoR) and the extracellular domain of VEGFR-1. When the engineered Ba/F3 cells are in the presence of an appropriate amount of VEGF-B, proliferation of the cells, as measured using an MTS dye reduction assay occurs. This is referred to as the VEGFR-1/EpoR/BaF3 proliferation assay. Anti-VEGF-B antibodies that inhibit binding of VEGF-B to VEGFR-1 inhibit VEGF-B induced cell proliferation in this assay.

Anti-VEGF-B antibodies that antagonize VEGF-B signaling through VEGFR-1 will inhibit VEGF-B-mediated activation of the reporter molecule in a reporter gene based assay such as that described by Scotney et al., supra.

Those skilled in the art appreciate that the cell based assays of the present invention, for example described above and in the Examples, may be utilised as a basis for screening for modulators of VEGF-B/receptor interaction. While such methods are well known to those skilled in the art, a brief description of the method is provided herein. The method involves subjecting appropriately engineered cells to a signal producing amount of VEGF-B under conditions where, in the absence of any antagonism of VEGF-B/receptor binding, a signal, for example proliferation or reporter luciferase expression, may be detected. The same experimental procedure is then conducted in the presence of one or more test compounds and the level of signal detected compared with that detected in the absence of a test compound. Test compounds which alter the level of signal detected compared with that detected in the absence of a test compound are then selected for further study. Test compounds may include phage display libraries of antibody variable domains and the like, or panels of monoclonal antibodies against VEGF-B may be screened across the assay.

Treatment of VEGF-B associated diseases and disorders may be by the administration of pharmaceutical compositions comprising a VEGF-B antagonist, preferably antibodies of the present invention, and one or more pharmaceutically acceptable carriers and/or diluents.

Pharmaceutically acceptable carriers and/or diluents include any and all solvents, dispersion media, coatings, anti-bacterial and antifungal agents, agents used for adjusting tonicity, buffers, chelating agents, and absorption delaying agents and the like. The use of such media and agents is well known in the art. Except insofar as any conventional media or agent is incompatible with the active form, use thereof in the therapeutic compositions is contemplated. Supplementary active ingredients can also be incorporated into the compositions.

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include agents to adjust tonicity, for example, sugars or sodium chloride. Prolonged absorption of the injectable compositions can be brought about by the use in the compositions of agents delaying absorption, for example, aluminum monostearate and gelatin. The compositions may also include buffers and chelating agents.

Sterile injectable solutions are prepared by incorporating the active form in the required amount in the appropriate solvent and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active form plus any additionally desired ingredient.

The amount of active form in such therapeutically useful compositions is such that a suitable dosage will be obtained.

The compositions of the present invention are useful in modifying VEGF-B mediated conditions including but not limited to tumors, in particular solid tumors, and any other VEGF-B mediated diseases or conditions. Pre-cancerous conditions and dispersed tumors, such as for example, myelomas and lymphomas may also be treated.

The human and humanized antibodies of the present invention and in particular humanized forms of the mAbs 1C6, 2H10, 4E12 and 2F5 are useful in the treatment of such conditions. Any adverse condition resulting from VEGF-B interaction with VEGF-B receptor may be treated by the administration of the antibodies of the present invention such as humanized forms of the mAbs selected from 1C6, 2H10, 4E12 and 2F5.

Accordingly, another aspect of the present invention contemplates a method for the treatment or prophylaxis of a condition mediated by VEGF-B such as but not limited to a cancer, said method comprising administering to a subject in need a therapeutically effective amount of a VEGF-B antagonist, for example an antibody, such as humanized form of a mAb selected from 1C6, 2H10, 4E12 and 2F5, for a time and under conditions sufficient to inhibit VEGF-B signaling through a VEGF-B receptor.

The type of tumors contemplated for treatment using the method and compositions of the present invention include without being limited to breast tumors, colorectal tumors, adenocarcinomas, mesothelioma, bladder tumors, prostate tumors, germ cell tumor, hepatoma/cholongio, carcinoma, neuroendocrine tumors, pituitary neoplasm, small round cell tumor, squamous cell cancer, melanoma, atypical fibroxanthoma, seminomas, nonseminomas, stromal leydig cell tumors, sertoli cell tumors, skin tumors, kidney tumors, testicular tumors, brain tumors, ovarian tumors, stomach tumors, oral tumors, bladder tumors, bone tumors, cervical tumors, esophageal tumors, laryngeal tumors, liver tumors, lung tumors, vaginal tumors and Wilm's tumor.

Dosage regimens may be adjusted to provide the optimum desired response (e.g., a therapeutic response). For example, a single bolus may be administered, several divided doses may be administered over time or the dose may be proportionally reduced or increased as indicated by exigencies of the therapeutic situation. It is especially advantageous to formulate parenteral compositions in dosage unit form for ease of administration and uniformity of dosage.

A physician or veterinarian having ordinary skill in the art can readily determine and prescribe the effective amount of the pharmaceutical composition required. For example, the physician or veterinarian could start doses of the VEGF-B antagonists, such as an antibody of the present invention, employed in the pharmaceutical composition at levels lower than that required in order to achieve the desired therapeutic effect and gradually increase the dosage until the desired effect is achieved. In general, a suitable daily dose of a composition of the invention may be that amount of the compound which is the lowest dose effective to produce a therapeutic effect. Such an effective dose will generally depend upon the factors described above. It is preferred that administration be by injection, preferably proximal to the site of the target (e.g., tumor). If desired, the effective daily dose of a pharmaceutical composition may be administered as two, three, four, five, six or more subdoses administered separately at appropriate intervals throughout the day.

For therapeutic applications, the VEGF-B antagonists, such as anti-VEGF-B antibodies of the present invention, are administered to a mammal, preferably a human, in a pharmaceutically acceptable dosage form such as those discussed above, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes. The VEGF-B antagonists, such as the anti-VEGF-B antibodies, also are suitably administered by intra tumoral, peritumoral, intralesional, or perilesional routes, to exert local as well as systemic therapeutic effects. The intraperitoneal route is expected to be particularly useful, for example, in the treatment of ovarian tumors.

For the prevention or treatment of VEGF-B mediated diseases or conditions, the appropriate dosage of VEGF-B antagonists, such as an anti-VEGF-B antibody will depend on the type of disease to be treated, as defined above, the severity and course of the disease, whether the antagonist is administered for preventive or therapeutic purposes, previous therapy, the patient's clinical history and response to the antagonist, and the discretion of the attending physician. The antagonist may be suitably administered to the patient at one time or over a series of treatments.

Depending on the type and severity of the disease, about 1 μg/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 μg/kg to about 20 mg/kg or more, depending on the factors mentioned above. For repeated administrations over several days or longer, the treatment is repeated until a desired suppression of disease symptoms occurs. The progress of this therapy is easily monitored by conventional techniques and assays, including, for example, radiographic tumor imaging.

Preferably, the subject is a human. However, veterinary applications are also contemplated for livestock animals as well as companion animals. In such cases it would be necessary to prepare an appropriate antibody designed to avoid an immunogenic response to the antibody by the mammal.

The present invention provides a method for treating a VEGF-B mediated disease or condition in a human subject, said method comprising administering to said subject a therapeutically effective amount of a VEGF-B antagonist for a time and under conditions sufficient to produce a desired suppression of the disease or condition.

The present invention further contemplates the use of a VEGF-B antagonist in the manufacture of a medicament in the treatment or prophylaxis of cancer including tumor tissue and pre-cancerous tissue in a subject.

Preferably the VEGF-B antagonist for use in the above method is an antibody. Preferably the antibody is a monoclonal antibody, Preferred antibodies for use in the above method are those which bind human VEGF-B with a $K_D$ value of $1\times10^{-7}$ M or less; preferably $1\times10^{-8}$ M or less; even more preferably $1\times10^{-9}$ M or less; and most preferably $5\times10^{-9}$ M or less.

In a specific embodiment, therefore, the present invention provides a method for ameliorating the effects of VEGF-B mediated cancer in a human subject, said method comprising administering to said subject an effective amount of a humanized form of a mAb selected from 1C6, 2H10, 4E12 and 2F5 or an antibody with equivalent VEGF-B blocking activity for a time and under conditions sufficient to reduce the growth or spread of the cancer.

The present invention further contemplates the use of a humanized form of a mAb selected from 1C6, 2H10, 4E12 and 2F5 or antibody with equivalent VEGF-B blocking activity in the manufacture of a medicament for the treatment or prophylaxis of cancer in a subject.

The present invention is further described by the following non-limiting Examples.

Example 1

Preparation of VEGF Proteins

General

Human and murine VEGF-B proteins and VEGF-A proteins were produced according to the general methodology previously described for human VEGF-B $B_{10-108}$ (Scotney et al., 2002, supra, Scrofani et al, 2000, Protein Science, 9:2018-2025). This is described below in more detail for the production of murine VEGF-B $B_{10-108}$. Proteins produced using this methodology initially have an additional 16 amino acids at the N-terminus that incorporate a 6×His tag and a Genenase I cleavage site between the tag and the start of the actual VEGF-B amino acid sequence. Where desired, these additional amino acids are removed by enzymatic cleavage using the general procedure outlined below. The presence or absence of the tag and cleavage site on a protein is indicated as follows: 6×His.hVEGF-$B_{10-108}$ indicates a protein containing amino acids 10-108 of the mature human VEGF-B with the N-terminal tag and cleavage site. hVEGF-$B_{10-108}$ indicates the same protein without the N-terminal tag and cleavage site. Other proteins are represented using the same approach.

Production of murine 6×His.VEGF-B

Following generally the procedure of Scotney et al. (supra), murine VEGF-$B_{10-108}$ with a 6×His tag and a Genenase I cleavage (6×His.mVEGF-$B_{10-108}$) was produced as a recombinant protein by bacterial fermentation following transformation with 6×His.mVEGF-$B_{10-108}$pET-15b (pET-15b vector from Novagen USA Cat #70755-3) into the *E. coli* BL21-Codon-Plus-[DE3]-RP strain (Stratagene, USA). To determine expression levels, samples were collected pre- and 1, 2 and 3 hrs post-induction with IPTG and assessed by SDS-PAGE and Western blot using an anti-6×His mAb (murine mAb, QIAGEN USA). Bound mAb was visualized by autoradiography using RRP-conjugated secondary reagent (sheep anti-mouse antibody, Chemicon USA) together with a luminescence substrate (PerkinElmer USA).

Following cell lysis 6×His.mVEGF-$B_{10-108}$ was purified from *E. coli* inclusion bodies by metal affinity chromatography (nickel affinity, Amersham) under denaturing and reducing conditions. Fractions were eluted from the column using 6M urea, 10 mM Tris, 100 mM phosphate [pH of 4.5] and were analyzed using SDS-PAGE. Western blot analysis was also performed on the eluted fractions using an anti-6×His mAb. Bound mAb was visualized by autoradiography using a HRP-conjugated secondary reagent together with a luminescence substrate (PerkinElmer USA).

Purified 6×His.mVEGF-B from nickel affinity was diluted to 100 μg/ml in 6 M guanidine hydrochloride (gd), 100 mM Tris (pH 8.5), reduced by the addition of DTT to 20 mM and dialyzed against 1M gd, 100 mM Tris (pH 8.5), 5 mM cysteine and 1 mM cystine for 2 days. Refolded 6×His.m-VEGF-B was then dialyzed against 0.1 M acetic acid prior to purification by reverse phase HPLC (RP-HPLC, Zorbax 300 SB-C8 column 250×21 mm i.d.). The fractions containing predominantly dimeric material (as assessed by non-reducing SDS-PAGE) were pooled for assaying. Western blot analysis (SDS-PAGE under reducing conditions) was performed on the RP-HPLC fractions using an anti-6×His mAb. Bound mAb was visualized by autoradiography using a HRPO-conjugated secondary reagent together with a luminescence substrate. Note that when VEGF-B is refolded correctly the N-terminus of the protein is concealed and the anti-6×His mAb does not bind to the protein.

Analysis of the activity of purified, refolded 6×His.m-VEGF-$B_{10-108}$ was determined using the VEGFR-1/EpoR/BaF3 cell proliferation assay as described herein and demonstrated a dose dependant proliferation of the VEGFR-1/EpoR/BaF3 cells in response to recombinant 6×His.mVEGF-$B_{10-108}$, and the positive control proteins hVEGF-$A_{11-109}$, hVEGF-$B_{10-108}$ and 6×His.hVEGF-$B_{10-108}$.

Enzymatic Cleavage Procedure

Note that where indicated the N-terminal 6×His tag was removed from human VEGF-A and/or VEGF-B preparations by enzymatic cleavage as follows. Briefly, 5 mg of lyophilised tagged protein was resuspended in a minimum volume of 1 mM acetic acid (500 μl) and 100× volume (50 ml) of Genenase I digest solution (5 μg/ml Genenase I, 100 mM Tris-HCl, 5 mM CaCl2, 200 mM NaCl, 0.02% Tween-20) added. The material was incubated for 24 hrs at 21° C. with gentle mixing before being dialysed into 0.1 M acetic acid to stop the reaction. The digested material was then purified by reverse phase chromatography and stored as lyophilised aliquots as previously described (Scotney et al., supra).

Example 2

Human VEGF-B Specific Mouse Monoclonal Antibodies Antagonise the Activity of VEGF-B in Cell-Based and Biochemical Assays Monoclonal antibodies were raised against recombinant human (h) VEGF-B isoforms using standard procedures (see Harlow and Lane, *Antibodies—A Laboratory Manual*, Cold Spring Harbour Laboratory, Chapter 6, 1988). Briefly, BALB/c or C57BL/6 mice were immunised via the intraperitoneal (i.p) route with approximately 10-30 μg of hVEGF-B (one of either hVEGF-$B_{167}$, hVEGF-$B_{10-108}$ or hVEGF-$B_{186}$ with or without an N-terminal 6×His tag) emulsified in complete Freunds Adjuvant (CFA) for the first immunisation and incomplete Freunds Adjuvant for subsequent immunisations (at least 2, and no less than 3-4 weeks apart). Three days prior to fusion and at least 3-4 weeks after the final i.p. immunisation mice were boosted with approximately 10 μg of hVEGF-B in phosphate buffered saline (PBS) via the intravenous (i.v.) route. Following fusion of spleen cells to the Sp2/O-Ag14 myeloma fusion partner and subsequent HAT (hypoxanthine, aminopterin and thymidine) selection, hybridomas secreting hVEGF-B specific mAbs were identified by ELISA and, after expansion, cloned by limit dilution on at least two occasions.

Cell Based Assay

Monoclonal Abs were assessed for antagonist activity using a novel VEGFR-1/EpoR/BaF3 proliferation assay. This assay is based on engineered BaF3 (DSMZ, Cat No. ACC 300) cells expressing a chimeric receptor incorporating the intracellular domain of the human erythropoietin receptor (EpoR) and the extracellular domain of VEGFR-1. VEGFR-1 ligands such as VEGF-A and VEGF-B trigger dimerisation of the chimeric receptor—the subsequent phosphorylation of the cytoplasmic domain of the EpoR leads to the activation of downstream signal transduction molecules and proliferation of the BaF3 cells. This approach has been used to develop proliferation-based biological assays for a number of cytokines and growth factors (for examples see Murayama et al., *J Biol, Chem.,* 269, 5976-5980, 1994; Fukada et al., *Immunity* 5, 449-460, 1996; Stacker et al., *J. Biol. Chem.,* 274, 34884-34892, 1999). The engineered BaF3 cells are maintained in DMEM (Invitrogen, USA) supplemented with 10% FCS, Zeocin (250 μg/ml, Invitrogen, USA), hVEGF-$A_{165}$ (50 ng/ml) pencillin (50 units/ml, Invitrogen, USA), streptomycin (50 μg/ml, Invitrogen, USA) and GlutaMAX-I (2 mM, Invitrogen, USA).

For analysis of mouse mAb antagonist activity washed VEGFR-1/EpoR/BaF3 cells ($5\times10^4$ cells/well, flat bottom 96 well microtitre plates) were pre-incubated with titrating test mAb for 1 hr prior to the addition of the indicated concentration of hVEGF-$A_{165}$, hVEGF-$B_{167}$ or hVEGF-$B_{10-108}$ for 72 hrs at 37° C. with 10% $CO_2$ in air. After 72 hrs, proliferation was assessed using an MTS dye reduction assay (Mosmann, T., *J. Immunol Methods,* 65, 55-63, 1983). The results demonstrated that mAbs 2H10, 4E12, 2F5 and 1C6 were able to antagonise the activity of hVEGF-$B_{167}$ (VB167) and hVEGF-$B_{10-108}$ (VB108) but not hVEGF-$A_{165}$ (VA165).

Biochemical Assay

The ability of monoclonal antibodies to block binding of VEGF-B to a ligand-binding fragment of VEGFR-1 was measured in a novel competition ELISA. A recombinant fragment of VEGFR-1, corresponding to the second Ig-like domain (D2-VEGFR-1, see Scotney et al., supra; Weismann et al., *Cell* 91, 695-704, 1997), was used to coat microtitre plates. A fixed, subsaturating concentration of recombinant hVEGF-$B_{10-108}$ (5 nM), which had been pre-incubated with serial dilutions of test mAb, was then incubated in these plates. After 1 hr, plates were washed and successively treated with rabbit anti-human VEGF-$B_{167}$ serum, mouse anti-rabbit-Ig horse radish peroxidase conjugate, and TMB substrate. The ELISA signal, measured colourimetrically at 450 nm after acid quenching, was proportional to the amount of VEGF-$B_{10-108}$ captured by plate-bound D2-VEGFR-1. Dose-dependent inhibition of binding by mAb was indicative of competition between mAb and D2-VEGFR-1 for binding to VEGF-$B_{10-108}$. The results of the assay revealed that mAbs 2H10, 1C6 and 2F5, but not 4E12, can antagonise binding of VEGF-$B_{10-108}$ to D2-VEGFR-1. The data suggest that antagonist mAb 4E12 binds to an area of VEGF-B not involved in the direct interaction with D2-VEGFR-1.

Example 3

Kinetics Analysis of Human VEGF-B Specific Antagonist Mouse Monoclonal Antibodies Kinetic Analysis A Biosensor-based approach was used for kinetic analysis of mAb binding to target VEGF-B using a BIAcore™ 2000 surface plasmon resonance instrument (Biacore AB, Uppsala, Sweden). A biosensor chip was activated for covalent coupling of VEGF-B using N-ethyl-N'-(3-dimethylaminopropyl)-carbodiimide hydrochloride (EDC) and N-hydroxysuccinimide (NHS) according to the supplier's (Biacore AB, Uppsala, Sweden) instructions. A solution of 5 μg/ml VEGF-$B_{10-108}$ in 20 mM sodium acetate, pH 4.8 was prepared and an aliquot (35 μl) was injected at a flow rate of 2 μl/min to achieve approximately 500-600 response units (RU) of coupled protein. Finally, 1 M ethanolamine was injected as a blocking agent.

For kinetics measurements, two-fold serial dilutions of test antibody starting at 125n M to 0.98 nM were injected in BIAcore™ buffer (20 mM HEPES, pH 7.8, 0.15 M NaCl, 3.4 mM EDTA, 0.005% Tween-20) with 1 mg/ml bovine serum albumin (BSA) at 25° C. at a flow rate of 15 μl/min. Simultaneous analysis of association ($k_a$) and dissociation ($k_d$) rate constants using BIAevaluation™ V3.02 software (Biacore AB, Uppsala, Sweden) was used to determine the equilibrium binding constant ($K_D$). Binding by each test mAb was assessed in duplicate and a summary of the data generated to date is presented in Table 3.

TABLE 3

| | Human VEGF-$B_{10-108}$ binding | | |
|---|---|---|---|
| mAb | ka (M − 1 · s − 1) | kd (s − 1) | KD (nM) |
| 1C6 | 5.45 x 104 | 1.53 x 10 − 4 | 2.82 |
| 2F5 | 1.34 x 105 | 1.14 x 10 − 4 | 0.86 |
| 2H10 | 3.85 x 105 | 6.77 x 10 − 5 | 0.18 |
| 4E12 | 4.87 x 104 | 1.32 x 10 − 4 | 2.71 |

Example 4

Monoclonal Antibodies Raised Against Human VEGF-B Cross React with, and Inhibit the Activity of, Mouse VEGF-B Monoclonal antibodies raised against hVEGF-B were tested for cross-reactivity with mVEGF-B using a standard ELISA format. mAbs were incubated with plate bound hVEGF-$B_{10-108}$ or 6×His.mVEGF-$B_{10-108}$ at a concentration of 1.25 μg/ml and bound mAb visualized using a HRP-conjugated secondary reagent and TMB substrate. Results demonstrate that only mAb 4E12 did not interact with both human and murine VEGF-B.

Cross-reactivity was further verified by Western blot analysis. 500 ng of $hVEGF_{10-108}$ and 6×His.mVEGF-$B_{10-108}$ were run on a non-reducing SDS-PAGE and transferred to PVDF membrane using standard procedures. Blots were probed with the test mAbs (2F5, 2H10 or 4E12) or a negative control mAb (6A9) at a concentration of 10 μg/ml. The bound mAbs were visualized by autoradiography using HRP-conjugated secondary reagent together with a luminescence substrate. mAbs 2F5 and 2H10 bound both human and murine VEGF-$B_{10-108}$, while mAb 4E12 bound only hVEGF-B.

mAbs 2H10, 1C6, 2F5 and 4E12 were also tested for their ability to inhibit the proliferative activity of 1 nM hVEGF-A, 50 nM 6×His.hVEGF-$B_{10-108}$ and 50 nM 6×His.mVEGF-$B_{10-108}$ using the VEGFR-1/EpoR/BaF3 proliferation assay as previously described. mAbs 2H10, 1C6 and 2F5 inhibited activity of both human and murine 6×His.VEGF-$B_{10-108}$, while mAb 4E12 was active only against the human form of VEGF-$B_{10-108}$.

Example 5

Detection of VEGF-B in Human Tumor Cell Line Conditioned Medium

The human tumor cell lines, 2008 (ovarian), A431 (epidermoid carcinoma), H460 (non-small cell lung), HT-29 (colon), MDA-MB-231 (breast) and PC-3 (prostate) were obtained from the Peter MacCallum Cancer Centre. The cell lines were routinely passaged as adherent cells in RPMI media (Invitrogen, USA) supplemented with 10% fetal calf serum (FCS), penicillin (50 units/ml, Invitrogen, USA) and streptomycin (50 μg/ml, Invitrogen, USA) and GlutaMAX (Invitrogen, USA) at 37° C. with 5% $CO_2$ in air. For analysis of VEGF-B production cell lines were diluted approximately 1:20 from a confluent culture into 100 mm petridishes containing 8.0 ml of media with or without heparin (100 μg/ml, Sigma, USA). Culture supernatants were recovered by centrifugation after 14 days and total VEGF-B protein level (VEGF-$B_{167}$ plus VEGF-$B_{186}$ isoforms) assessed a standard sandwich ELISA assay. The sandwich ELISA was based on microtitre plate bound anti-VEGF-B mAb (VEGF-$B_{167}$ and VEGF-$B_{186}$ reactive), with captured VEGF-B detected using a rabbit anti-VEGF-B polyclonal antibody and, subsequently, a HRP-conjugated anti-rabbit Ig reagent (Chemicon). Test VEGF-B was quantitated using a standard curve established with recombinant VEGF-B protein.

All human tumor cell lines assessed were demonstrated to express VEGF-B. The VEGF-$B_{167}$ isoform retains a C-terminal heparin binding domain and, as a result, a proportion of expressed protein is known to remain cell-associated. Heparin was included in the culture media in order to release this material from the cell surface and in some cases this resulted in slightly higher levels of VEGF-B detected in the cell supernatant.

Example 6

Human Tumor Cell Line HT-29 Mouse Xenograft Study

Novel therapeutics agents that potentially limit the growth of human tumors can be assessed for efficacy in vivo using well characterised mouse xenograft models. As described above in Example 5 a number of human tumor cell lines, all of which grow as solid tumors when grafted into immunodeficient mice, express VEGF-B protein.

Human colon carcinoma HT-29 tumor cells growing exponentially in vitro were harvested, washed and injected ($5\times10^6$/mouse) into the subcutaneous tissue of the right hindlimb of an anesthetized athymic nude mice. Treatment was commenced when tumors reached a size of approximately 100 $mm^3$ (approximately 2 weeks) at which point mice were divided into treatment groups of 10 animals. For analysis of anti-VEGF-B mAb 2H10, one group of 10 mice was treated twice weekly with an intraperitoneal (ip) injection of approximately 400 μg of test 2H10 in a volume of 200 μl, while a second group of mice was treated with the identical amount of an isotype matched control mAb (mAb C44, colchicine specific, ATCC Cat No. CRL-1943). Treatment was continued for a period of 5-7 weeks and the width and length of tumors was determined at regular intervals (for example every 4-5 days) using electronic calipers. Tumor volume ($mm^3$) was calculated according to the formula: $0.5\times\text{length}\times\text{width}^2$.

By day 38 post initiation of treatment, there was a 41% reduction in tumor volume in mice treated with the anti-VEGF-B mAb 2H10 when compared with tumors in the mice treated with the isotype matched control mAb. This compares favourably with the anti-tumor activity observed for a mAb directed against VEGF-A using human colon carcinoma HT-29 tumor cells in a similar tumor xenograft model (Asano, M et al, *Jpn J Cancer Research,* 90(1): 3-100, 1999).

Example 7

Cloning of mAb 2H10 Variable Region Genes for the Generation of a Therapeutic Humanized mAb Messenger RNA was prepared from hybridoma cells producing 2H10 mAb, and the variable region sequences were reverse transcribed and amplified by RT-PCR. Partially degenerate PCR primers based on the N-terminal amino acid sequence and the antibody isotype were used to amplify the light chain variable region. The heavy chain variable region was amplified using a forward primer designed to anneal to sequence encoding the N-terminal leader peptide, and a reverse primer based on the antibody isotype (Coloma et al 1991, Larrick et al. 1989). The subsequent PCR products were sequenced to reveal the amino acid sequence of the variable regions of 2H10. The amino acid sequences of the variable regions of antagonist mAbs 4E12 and 2F5 were determined using an identical strategy (see Table 1; FIGS. 8-10)

Example 8

Human Tumor Cell Line DU145 Mouse Xenograft Study

As noted in Example 6 novel therapeutics agents that potentially limit the growth of human tumors can be assessed for efficacy in vivo using well characterised mouse xenograft models.

Hunan prostate carcinoma DU145 tumor cells growing exponentially in vitro were harvested, washed and injected ($2\times10^6$ in 1:1 PBS:Matrigel/mouse) into the subcutaneous tissue of the right flank of an anesthetized SCID mice. Treatment was commenced when tumors reached a size of approximately 100 $mm^3$ at which point mice were divided into treatment groups of 10 animals. For analysis of anti-VEGF-B mAb 2H10, one group of 10 mice was treated twice weekly with an intraperitoneal (ip) injection of approximately 400 μg of test 2H10 in a volume of 200 μl, while a second group of mice was treated with the identical amount of an isotype matched control mAb (mAb C44, colchicine specific, ATCC Cat No. CRL-1943). Treatment was continued for a period of 4-5 weeks and the width and length of tumors was determined at regular intervals (for example every 4-5 days) using electronic calipers. Tumor volume ($mm^3$) was calculated according to the formula: $0.5\times length\times width^2$.

By day 33 post initiation of treatment, there was a significant reduction in tumor volume in mice treated with the anti-VEGF-B mAb 2H10 when compared with tumors in the mice treated with the isotype matched control mAb. The level of reduction in tumor growth was similar to that observed for the HT-29 tumor experiments described above.

Example 9

Human Tumor Cell Line A431 Mouse Xenograft Study

As noted in Example 6 novel therapeutics agents that potentially limit the growth of human tumors can be assessed for efficacy in vivo using well characterised mouse xenograft models.

Human squamous cell carcinoma A431 tumor cells growing exponentially in vitro were harvested, washed and injected ($3\times10^6$ in 1:1 PBS:Matrigel/mouse) into the subcutaneous tissue of the right flank of an anesthetized athymic nude mice. Treatment was commenced when tumors reached a size of approximately 100 $mm^3$ at which point mice were divided into treatment groups of 10 animals. For dose-response analysis of anti-VEGF-B mAb 2H10, groups of 10 mice were treated twice weekly with an intraperitoneal (ip) injection of approximately 1000 μg, 400 μg, 40 μg or 4 μg of test 2H10 in a volume of 200 μl, while a fifth group of mice was treated twice weekly with an ip injection of 1000 μg of an isotype matched control mAb (mAb C44, colchicine specific, ATCC Cat No. CRL-1943). Treatment was continued for a period of 17 days and the width and length of tumors was determined at regular intervals (for example every 2-3 days) using electronic calipers. Tumor volume ($mm^3$) was calculated according to the formula: $0.5\times length\times width^2$.

By day 17 post initiation of treatment, there was a significant reduction in tumor volume in mice treated with the anti-VEGF-B mAb 2H10, with the extent of reduction proportional to the dose of 2H10 administered (ie. level of reduction of tumor growth: 1000 μg dose>400 μg dose>40 μg dose>4 μg dose). When compared with the 4 μg/dose group, the level of reduction in tumor growth observed with 1000 μg/dose was approximately 40-45%. Compared with the 4 μg dose of 2H10, control mAb C44 at 1000 μg dose appeared to cause some non-specific reduction in tumor growth.

Example 10

Humanisation of Anti-VEGF-B mAb 2H10

Generation of CDR-grafted Fabs and mouse-human chimeric Fabs

The VBASE database (database of human antibody genes http://vbase.mrc-cpe.cam.ac.uk/) was used to identify human germline variable region sequences closely related to the 2H10 variable region sequences described in Example 7 and shown in FIG. 1. The EMBL database sequences X93622 and 300242 (human unrearranged germline antibody light chain regions PK9 and JK4 respectively) and HSIGDP75 and J00256 (human unrearranged germline antibody heavy chain regions DP75 and JH4a respectively) (FIG. 4) were selected for subsequent CDR grafting.

Nucleic acid sequences encoding 2H10 CDR-grafted human germline Fab (CDR-Fab) were prepared by replacing the nucleotides encoding the CDRs of the human germline variable region sequences with the nucleotide sequences for the 2H10 CDRs (FIG. 5). The variable region sequences were then fused to nucleotide sequences encoding the corresponding human constant domains of the light and heavy chains to give cDNAs encoding the CDR-Fab. The CDR-Fab nucleotide sequences were modified to optimise the codons for expression in *E. coli* and then inserted into a single *E. coli* expression vector to generate a dicistronic construct to express soluble functional CDR-Fabs. For a general description of the expression of antibody fragments in *E. coli* refer to Corisdeo S, and Wang B. (2003), Functional expression and display of an antibody Fab fragment in *Escherichia coli*: study of vector design and culture conditions. Protein Expression and Purification 34: 276-279.

FIG. 6 shows the nucleic acid sequences for the 2H10 CDR regions optimised for expression in *E. coli.*

A mouse-human chimeric Fab, (consisting of the murine 2H10 heavy and light chain variable regions fused to the corresponding human constant domains), and a soluble 2H10 murine Fab protein, (prepared by the proteolytic digestion of the full length murine 2H10 antibody using the papain digestion protocol described in "Antibody Production: Essential Techniques" Peter J. Delves, 1997, John Wiley & Sons, Chichester, UK) were also prepared for VEGF-B binding studies. The mouse-human chimeric Fab and the 2H10 murine Fab had similar binding affinity for VEGF-B and were used to assess whether the CDR-Fab required framework optimization to optimize the presentation of the murine CDRs by the human framework and improve VEGF-B binding affinity.

Comparison of the Binding Affinities of the Chimeric and CDR-Grafted Fabs

The binding affinity of the CDR-Fab for VEGF-B may be compared to the VEGF-B binding affinity of the mouse-human chimeric Fab and the 2H10 murine Fab in a number of ways, such as in competition-based binding assays (for example, as phage displayed Fabs in an ELISA format) or as purified soluble protein by Biacore analysis.

The binding affinity of the CDR-Fab for immobilised human VEGF-B was compared with the 2H10 murine Fab by measuring surface plasmon resonance (SPR) using a BIAcore instrument. The association rate constant ($k_{on}$), the dissociation rate constants ($k_{off}$), and the equilibrium binding constants ($K_D$) were calculated for the CDR-Fab and the 2H10 murine Fab using data from injections of each Fab at several different concentrations. The CDR-Fab was found to have a faster dissociation rate than the 2H10 murine Fab, resulting in a weaker binding affinity for VEGF-B (Table 4). Optimisation of key framework residues was therefore undertaken to improve the binding affinity of the CDR-Fab.

The variable region sequences of the CDR-Fab and the mouse-human chimeric Fab were aligned to identify framework residues within the CDR-Fab which may require optimization (Foot J. and Winter G. (1992) Antibody Framework Residues Affecting the Conformation of the Hypervariable Loops. J. Mol. Biol. 224: 487-499). Six key framework residues were identified, these being L71, H67, H69, H71, H73 and H75. A panel of twelve CDR-Fab framework variants were generated by individual and combined changes of the key framework residues back to the original murine sequence (six single backmutations and pairs of H67, H69, H71 and H73).

The twelve CDR-Fab framework variants were expressed in *E. coli* and their dissociation rates were compared to the dissociation rates for the mouse-human chimeric Fab and the CDR-Fab by BIAcore. CDR-Fab variants with the H73 backmutation, either alone or in combination with one of H67, H69 OR H71, were found to have similar dissociation rates to the mouse-human chimeric Fab (Table 5).

The binding affinities of the four H73CDR-Fab framework variants (H73, H67/73, H69/73 AND H71/73) were then compared with the murine-human chimeric Fab in a competition ELISA. These FIVE Fabs were tested in solution for their ability to bind to plate bound human VEGF-B (1 ug/ml) in the presence of titrating amounts of VEGF-B in solution, and the IC50s were determined (the soluble VEGF-B concentration at which 50% binding to immobilised VEGF-B is displaced). The IC50 for each CDR-Fab variant and the murine-human chimeric Fab was used to rank the VEGF-B binding affinity. The CDR-Fab variant with the single H73 backmutation was found to have the highest VEGF-B binding affinity, similar to that of the murine-human chimeric Fab (Table 5).

The equilibrium binding constant ($K_D$) of the H73 CDR-Fab framework variant for immobilised human VEGF-B was then determined by BIAcore and found to be within 3-fold of the equilibrium binding constant for the 2H10 murine Fab (337 pM compared with 115 pM respectively).

TABLE 4

| | $K_D$ | kon | koff |
|---|---|---|---|
| 2H10 Murine Fab | 115 pM | $8.52 \times 10^5$ | $9.42 \times 10^5$ |
| CDR- Fab | 660 pM | $8.40 \times 10^5$ | $5.55 \times 10^4$ |

TABLE 5

| CDR-Fab Variant | Off Rate (koff) | Relative $k_{off}$ $k_{off}$CDR-Fab variant/$k_{off}$ murine-human chimera | *Relative VEGF-B binding affinity |
|---|---|---|---|
| Murine-Human Chimera | $3.87 \times 10^{-5}$ | 1.0 | 1.0 |
| L71 | $8.1 \times 10^{-5}$ | 2.1 | |
| H67 | $1.27 \times 10^{-4}$ | 3.3 | |
| H69 | $1.11 \times 10^{-4}$ | 2.9 | |
| H71 | $1.11 \times 10^{-4}$ | 2.9 | |
| H73 | $5.55 \times 10^{-5}$ | 1.4 | 1.415 |
| H75 | $1.23 \times 10^{-4}$ | 3.2 | |
| H67/69 | $1.34 \times 10^{-4}$ | 3.5 | |
| H67/71 | $1.37 \times 10^{-4}$ | 3.6 | |
| H67/73 | $6.3 \times 10^{-5}$ | 1.6 | 1.685 |
| H69/71 | $1.34 \times 10^{-4}$ | 3.5 | |
| H69/73 | $6.85 \times 10^{-5}$ | 1.8 | 1.475 |
| H71/73 | $5.67 \times 10^{-5}$ | 1.5 | 2.075 |
| CDR-Fab | $1.42 \times 10^{-4}$ | 3.7 | 2.25 |

*measured by competition ELISA, where relative binding affinity is equal to $IC_{50}$ CDR-Fab variant/$IC_{50}$ murine-human chimera.

BIBLIOGRAPHY

Aase, K. et al., *Circulation* 104:358-364, 2001
Altschul, S. F., et al., *J. Mol. Biol.* 215:403-410, 1990
Altschul, S. F., *J. Mol. Biol.* 219:555-565, 1991
Altschul, S. F., et al., *Nucleic Acids Res.* 25:3389-3402, 1997
Asano, M et al, *Jpn J Cancer Research,* 90(1): 3-100, 1999
Ausubel F. M et al. (eds.), Current Protocols in Molecular Biology, John Wiley & Sons, Inc, 1994
Bellomo, D. et al., *Circ. Res.* 86:E29-E35, 2000
Benjamin, L. E. & Keshet, E., *Proc Natl Acad Sci USA* 94:8761-6, 1997
Benoist, et al., *Nature* 290:304-310, 1981
Bird, *Science* 242: 423, 1988
Carmeliet, P. et al., *Nature* 407:249-57, 2000
Carmeliet, P. et al., *Nature* 380:435-9, 1996
Chothia and Lesk, *J. Mol. Biol.* 196:901-917, 1987
Clackson et al., *Nature* 352:624-628, 1991
Clauss, M. et al., *J. Biol. Chem.* 271:17629-17634, 1996
Coloma et al., *Biotechniques,* 11(2):152-156, 1991
Corisdeo S. and Wang B., *Protein Expression and Purification* 34:270-279, 2003
Delves, P. J., Antibody Production: Essential Techniques, John Wiley & Sons, Chichester, UK, 1997
de Vries, C. et al., *Science* 255:989-991, 1992
Dvorak, H. F et al., *Curr Top Microbiol Immunol* 237:97-132, 1999
Dvorak, H. F., *Semin Perinatol* 24:75-8, 2000
Eriksson, U. & Alitalo, K., *Curr Top Microbiol Immunol* 237:41-57, 1999
Ferrara, N & Davis-Smyth, T, *Endocr. Rev* 18.14-25, 1997
Ferrara, N et al., *Nat. Med.* 9:669-676, 2003
Ferrara, N. & Alitalo, K, *Nat Med* 5:1359-64, 1999
Ferrara, N. et al., *Nature* 380:439-42, 1996
Folkman, J, *Nat Med* 1:27-31, 1995
Folkman, J & Klagsbrun, M, *Science* 235:442-447, 1987
Fong, G. H. et al., *Development* 126:3015-3025, 1999

Foot J. and Winter G., *J. Mol. Biol.* 224:487-499, 1992
Fukada et al., *Immunity* 5:449-460, 1996
Gerber, H-P et al., *J. Biol. Chem.* 272:23659-23667, 1997
Glover D. N. (ed.), DNA Cloning: A Practical Approach, Volumes I and II, 1985
Hanahan, D. & Folkman, *J. Cell* 86:353-64, 1996
Harlow and Lane (eds.), Antibodies: A Laboratory Manual, Cold Spring Harbor Laboratory Press, Cold Spring Harbor, N.Y., 1988
Huston et al., *Proc. Natl. Acad. Sci. USA* 85:5879, 1988
Hiratsuka, S. et al., *Proc. Natl. Acad. Sci. USA* 4:9349-9354, 1998
Jones et al., *Nature* 321:522-525, 1986
Kabat et al. in Sequences of Proteins of Immunological Interest, 5th Ed., US Dept. of Health and Human Services, PHS, NIH, NIH Publication No. 91-3242, 1991
Kennet et al. (eds.), Monoclonal Antibodies, Hybridomas: A New Dimension in Biological Analyses, Plenum Press, New York, 1980
Keyt, B. et al., *J. Biol. Chem.* 271:5638-5646, 1996
Klagsbrun, M. et al., *Ann. Rev. Physiol.* 53:217-239, 1991
Kohler et al., *Nature* 256:495, 1975
Kortt et al., *Protein Engineering* 10:423, 1997
Larrick et al., *Bio/Technology* 7:934, 1989
Li, X et al., *Growth Factors* 19:49-59, 2001
Liu et al., *Proc. Natl. Acad. Sci. USA* 84:3439, 1987
Makinen, T. et al., *Nat Med* 7:199-205, 2001
Marks et al., *J. Mol. Biol.* 222:581-597, 1991
Maxam and Gilbert, *Proc. Natl. Acad. Sci. USA* 74(2):560-564, 1977
Morrison et al., *Proc. Natl. Acad. Sci. USA* 81:6851-6855, 1984
Mosmann, T., *J. Immunol Methods,* 65:55-63, 1983
Murayama et al., *J. Biol, Chem.,* 269:5976-5980, 1994
Neufeld, G et al., *Trends Cardiovasc Med* 12:13-19, 2002
Niida, S. et al., *J. Exp. Med.* 190:293-298, 1999
Olofsson et al., J Biol. Chem. 271:19310-19317, 1996
Olofsson et al., *Curr Opin in Biotech. Vol* 10:528-535, 1999
Park, J et al., *J Biol. Chem.* 269:25646-25654, 1994
Presta, *Curr. Op. Struct. Biol.* 2:593-596, 1992
Rahimi, N et al., *J. Biol. Chem.* 275:16986-16992, 2000
Reichmann et al., *Nature* 332:323-329, 1988
Saiki, et al., *Science* 239: 487, 1988
Salven, P. et al. (1998) Am J Pathol, 153: 103-108
Sambrook, Fritsch & Maniatis, Molecular Cloning: A Laboratory Manual, Second Edition Cold Spring Harbor Laboratory Press, Cold Spring Harbor, N.Y., 1989
Sanger, et al., *Proc. Natl. Acad. Sci. USA* 74(12):5463-5467, 1977
Scotney et al., *Clin Exp Pharmacol Physiol* (*Australia*), 29(11):1024-1029, 2002
Scrofani et al, *Protein Science,* 9:2018-2025, 2000
Skobe, M. et al., *Nat Med* 7:192-8, 2001
Soker, S et al., *Cell* 92:735-45, 1998
Stacker, S. A. et al., *Nat Med* 7:186-91, 2001
Stacker et al., *J. Biol. Chem.,* 274:34884-34892, 1999
Waltenberger, J. et al., *J. Biol. Chem.* 269:26988-26995, 1994
Wang, H & Keiser, J, *Circ. Res.* 83:832-840, 1998
Ward et al., *Nature* 334:544, 1989
Weismann et al., *Cell* 91:695-704, 1997
Winter and Harris, *TIPS* 14:139, 1993
Yancopoulos, G. D. et al., *Nature* 407:242-248, 2000

The invention claimed is:

1. An isolated anti-VEGF-B antibody that inhibits binding of VEGF-B to VEGFR-1 wherein the antibody binds human VEGF-B with a $K_D$ value of $1\times10^{-7}$M or less, wherein said antibody comprises all six CDR sequences from the heavy and light chain variable regions of mAb 2H10 as set forth in SEQ ID NOs: 5-10 in a human framework with a backmutation at position H73.

2. An antigen-binding fragment of an antibody of claim 1, wherein the fragment binds to VEGF-B.

3. The antigen-binding fragment of claim 2 wherein the antigen-binding fragment is selected from a Fv, Fab, $F(ab')_2$, a single chain Fv fragment, a disulphide stabilized Fv fragment, a minibody and a diabody.

4. The antigen binding fragment of claim 3 wherein the single chain Fv fragment is a sFv or scFv.

5. The antibody of claim 1 or an antigen-binding fragment of said antibody wherein the antibody or antigen-binding fragment is cross-reactive for human VEGF-B and VEGF-B from at least one other mammal.

6. The antibody or antigen-binding fragment of claim 5 wherein the antibody or antigen-binding fragment is cross-reactive for human VEGF-B and murine VEGF-B.

7. The isolated anti-VEGF-B antibody of claim 1, wherein the antibody binds human VEGF-B with a $K_D$ value of $1\times10^{-8}$M or less.

8. The isolated anti-VEGF-B antibody of claim 1, wherein the antibody binds human VEGF-B with a $K_D$ value of $1\times10^{-9}$M or less.

9. A composition comprising an antibody of claim 1.

10. An expression vector comprising a nucleic acid encoding the light chain of the antibody according to claim 1 and a nucleic acid encoding the heavy chain of the antibody according to claim 1, wherein said expression vector is capable of expressing the nucleic acids in prokaryotic or eukaryotic host cell.

11. A prokaryotic or eukaryotic host cell comprising an expression vector of claim 10.

12. A method for producing an anti-VEGF-B antibody comprising (a) culturing the prokaryotic or eukaryotic host cell of claim 11 for a period of time sufficient to allow for expression of the antibody and (b) purifying the expressed antibody.

13. An isolated anti-VEGF-B antibody according to claim 1 comprising a variable light chain sequence and a variable heavy chain having the sequences shown in SEQ ID NOs:29 and 30.

14. A composition comprising the antibody according to claim 13.

15. An expression vector comprising a nucleic acid encoding the light chain of the antibody according to claim 13 and a nucleic acid encoding the heavy chain of the antibody according to claim 13, wherein said expression vector is capable of expressing said nucleic acid in prokaryotic or eukaryotic host cell.

16. A prokaryotic or eukaryotic host cell comprising an expression vector of claim 15.

17. A method for producing an anti-VEGF-B antibody comprising (a) culturing the prokaryotic or eukaryotic host cell of claim 16 for a period of time sufficient to allow for expression of the antibody and (b) purifying the expressed antibody.

18. An isolated anti-VEGF-B antibody that inhibits binding of VEGF-B to VEGFR-1 wherein the antibody binds human VEGF-B with a $K_D$ value of $1\times10^{-7}$M or less, wherein said antibody comprises (a) all six CDR sequences from the heavy and light chain variable regions of mAb 2F5 as set forth in SEQ ID NOs: 21-26, or (b) all six CDR sequences from the heavy and light chain variable regions of mAb 106 as set forth in SEQ ID NOs: 45-50.

19. The isolated anti-VEGF-B antibody of claim 18, wherein the antibody binds human VEGF-B with a $K_D$ value of $1\times10^{-8}$M or less.

20. The isolated anti-VEGF-B antibody of claim 18, wherein the antibody binds human VEGF-B with a $K_D$ value of $1\times10^{-9}$M or less.

21. The antibody any of claims 18-20 wherein the antibody is a monoclonal antibody.

22. The antibody of claim 21 wherein the antibody is humanized.

23. An antigen-binding fragment of an antibody of claim 22, wherein the fragment binds to VEGF-B.

24. The antigen-binding fragment of claim 23 wherein the antigen-binding fragment is selected from a Fv, Fab, $F(ab')_2$, a single chain Fv fragment, a disulphide stabilized Fv fragment, a minibody and a diabody.

25. The antigen binding fragment of claim 24 wherein the single chain Fv fragment is a sFv or scFv.

26. A composition comprising the antibody of claim 21.

27. An expression vector comprising a nucleic acid encoding the light chain of the antibody according to claim 21 and a nucleic acid encoding the heavy chain of the antibody according to claim 21, wherein said expression vector is capable of expressing the nucleic acids in prokaryotic or eukaryotic host cell.

28. A prokaryotic or eukaryotic host cell comprising an expression vector of claim 27.

29. A method for producing an anti-VEGF-B antibody comprising (a) culturing the prokaryotic or eukaryotic host cell of claim 28 for a period of time sufficient to allow for expression of the antibody and (b) purifying the expressed antibody.

* * * * *